US005811397A

United States Patent [19]
Francavilla et al.

[11] Patent Number: 5,811,397
[45] Date of Patent: Sep. 22, 1998

[54] MAMMALIAN AUGMENTER OF LIVER REGENERATION AND VARIANTS THEREOF

[75] Inventors: Antonio T. Francavilla, Pittsburgh, Pa.; Michio Hagiya, Shiga, Japan; Thomas E. Starzl, Pittsburgh, Pa.

[73] Assignees: University of Pittsburgh, Pittsburgh, Pa.; Toyobo Co.,Ltd., Japan

[21] Appl. No.: 665,484

[22] Filed: Jun. 12, 1996

Related U.S. Application Data

[60] Division of Ser. No. 367,968, Jan. 3, 1995, Pat. No. 5,607,844, which is a continuation-in-part of Ser. No. 197,496, Feb. 16, 1994, Pat. No. 5,480,797, and Ser. No. 275,370, Jul. 15, 1994, Pat. No. 5,550,037.

[51] Int. Cl.[6] ......................... A61K 38/18; C07K 14/475
[52] U.S. Cl. ............................. 514/12; 530/350; 530/399
[58] Field of Search .................................. 530/350, 399; 514/12

[56] References Cited

U.S. PATENT DOCUMENTS 5,440,022  8/1995  Wu et al. ................................ 530/399

OTHER PUBLICATIONS

Yao et al., Hepatology 12:1144–1151, 1990.
Labrecque, Dig. Dis. Sci. 36:669–673, 1991.
Francavilla et al., Dig. Dis. Sci. 36:674–680, 1991.
Yao et al., Chin. Med. J. 106:527–532 (1993).
Zhou et al., Chin. Med. Sci. J. 7:197–200 (1992).
He et al., "Human Hepatic Stimulator Substance: A Product of Gene Expression of Human Fetal Liver Tissue," Hepatology, Feb. 1993, vol. 17, pp. 225–229.
Francavilla et al., "Extraction and Partial Purification of a Hepatic Stimulatory Substance in Rats, Mice, and Dogs," Cancer Research 47, 5600–5606, Nov. 1, 1987.
LaBrecque et al., "Purification and Physical–Chemical Characterization of Hepatic Stimulator Substance," Hepatology, vol. 7, No. 1, 1987, pp. 100–106.
Hagiya et al., "Cloning and sequence analysis of the rat augmenter of liver regeneration (ALR) gene: Expression of biologically active recombinant ALR and demonstration of tissue distribution," Proc. Natl. Acad. Sci. USA, vol. 91, pp. 8142–8146, Aug. 1994 pp. 8142–8146.

*Primary Examiner*—Eric Grimes
*Attorney, Agent, or Firm*—Cushman Darby & Cushman Intellectual Property Group of Pillsbury Madison & Sutro, LLP

[57] ABSTRACT

Full-length cDNA clones have been isolated encoding purified augmenter of liver regeneration (ALR) polypeptides prepared from the cytosol of livers from weanling rats and from humans. The full-length clone from the rat is a 1226 bp cDNA containing an 81 bp 5'-untranslated region, a 594 bp coding region and a 551 bp 3'-untranslated region. The coding region encodes three proteins with estimated molecular weights of 15,081, 20,193 and 22,835. The full-length clone from the human consists of a 727 bp cDNA containing a 4 bp 5'-untranslated region, a 615 bp coding region and a 108 bp 3'-untranslated region, including the termination codon TAG and the poly (A) region. The 615 bp coding region encodes four proteins, human ALR-V1, ALR-V2, ALR-V3 and ALR, having estimated molecular weights of 23,448, 20,834, 20,703 and 15,028, respectively.

11 Claims, 21 Drawing Sheets

```
                      10        20        30        40
hALR-cDNA-AA  MRTQQKRDTKFREDCPPDREELGRHSWAVLHTLAAYYPDL
              X:::::::  :::::::  :::::::  ::  ::::::::::
rALR-cDNA-AA  MRTQQKRDIKFREDCPQDREELGRNTWAFLHTLAAYYPDM
                      10        20        30        40

50        60        70        80
hALR-cDNA-AA  PTPEQQQDMAQFIHLFSKFYPCEECAEDLRKRLCRNHPDT
              ::::::::::::::  :::::::::::::::  :::  :  :::
rALR-cDNA-AA  PTPEQQQDMAQFIHIFSKFYPCEECAEDIRKRIDRSQPDT
                      50        60        70        80

90       100       110       120
hALR-cDNA-AA  RTRACFTQWLCHLHNEVNRKLGKPDFDCSKVDERWRDGWK
              ::   :  ::::  :::::::::::::::::::::  ::::::::::
rALR-cDNA-AA  STRVSFSQWLCRLHNEVNRKLGKPDFDCSRVDERWRDGWK
                      90       100       110       120 hALR-cDNA-AA  DGSCD
              ::::X
rALR-cDNA-AA  DGSCD
```

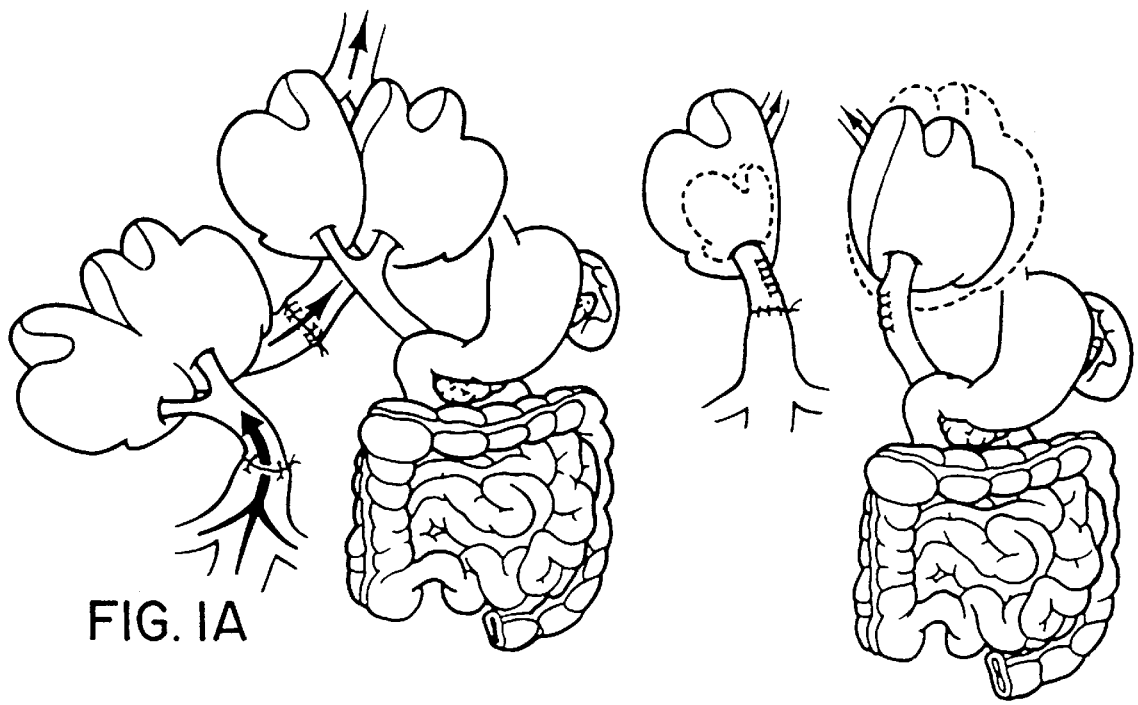
FIG. 1A
FIG. 1B
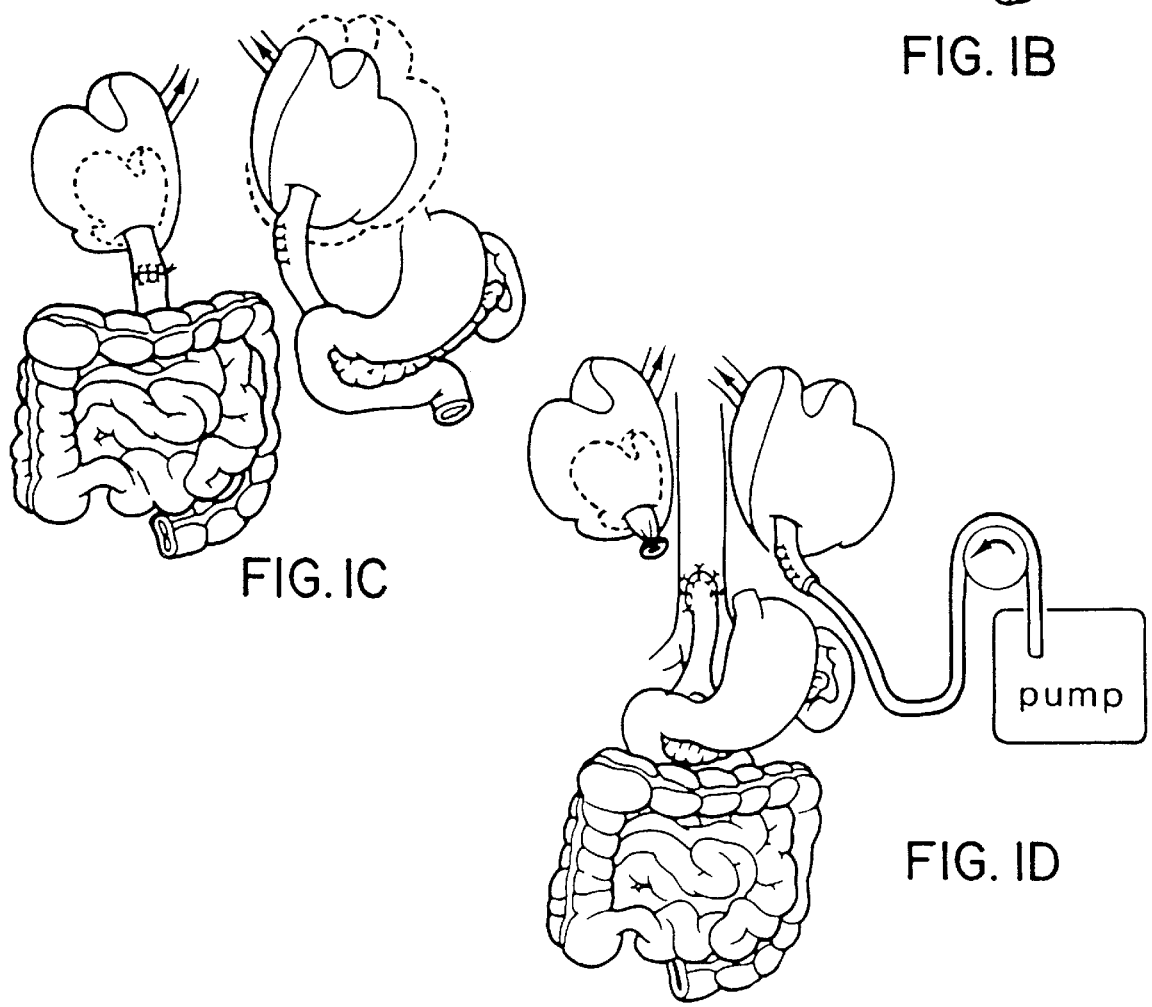
FIG. 1C
FIG. 1D

FIG.5

```
Met Arg Thr Gln Gln Lys Arg Asp Ile Lys Phe Arg Glu Asp Cys Pro
 1                   5                  10                  15

Gln Asp Arg Glu Glu Leu Gly Arg Asn Thr Trp Ala Phe Leu His Thr
                20                  25                  30

Leu Ala Ala Tyr Tyr Pro Asp Met Pro Thr Pro Glu Gln Gln Gln Asp
                35                  40                  45

Met Ala Gln Phe Ile His Ile Phe Ser Lys Phe Tyr Pro Cys Glu Glu
        50                  55                  60

Cys Ala Glu Asp Ile Arg Lys Arg Ile Asp Arg Ser Gln Pro Asp Thr
 65                  70                  75                  80

Ser Thr Arg Val Ser Phe Ser Gln Trp Leu Cys Arg Leu His Asn Glu
                85                  90                  95

Val Asn Arg Lys Leu Gly Lys Leu Pro Asp Phe Asp Cys Ser Arg Val Asp
                100                 105                 110

Glu Arg Trp Arg Asp Gly Trp Lys Asp Gly Ser Cys Asp
115                 120                 125
```

FIG. 6A

| | | | | | |
|---|---|---|---|---|---|
| CGCGGCGCTGG | CGGTGGCATG | CGGCGCTGCTC | TGTCCCGTCT | CCTGCACGCC | CTCTTGGCCC | 60 |
| CGCTGCTCGT | ACGCCAGCAA | TATGGCGGGCG | CCCAGCGAAC | CCGCAGGTTT | CCCTCGCGGC | 120 |
| AGTCGCTTCT | CCTTCCTGCC | GGGCGGGGCG | CACTCGGAGA | TGACCGACGA | CCTGGTGACT | 180 |
| GACGCGCGGG | GCCGCGGCGC | AAGGCATAGA | AAAGACAACG | CCCCTGCCGC | GGCCCCGGCG | 240 |
| CCGAAAGGTT | TGGAGCACGG | GAAGCGACCG | TGCCGGGCCT | GCGTGGACTT | CAAGTCGTGG | 300 |
| ATGCGGACCC | AGCAGAAGCG | GGACATCAAG | TTTAGGGAGG | ACTGTCCACA | GGATCGGGAA | 360 |
| GAATTGGGTC | GCAACACCTG | GGCTTTCCTT | CATACGCTGG | CCGCCTATTA | CCCGGACATG | 420 |
| CCCACGCCAG | AACAAACAGCA | GGATATGGCC | CAGTTCATAC | ATATATTTTC | CAAGTTTTAC | 480 |
| CCCTGTGAGG | AGTGTGCAGA | AGACATAAGG | AAGAGGATAG | ACAGGAGCCA | GCCAGACACA | 540 |
| AGCACTCGAG | TGTCCTTCAG | CCAGTGGCTG | TGCCGCCTTC | ACAATGAAGT | GAACCGGAAG | 600 |

FIG. 6B

```
CTGGGCAAGC CTGATTTGA  CTGCTCAAGA GTTGATGAGC GATGGCGTGA CGGCTGGAAG   660
GACGGCTCCT GTGACTAAGG ATTACCACAG ACCGTGCAGG GCAACGCCGG GTTCTATGGG   720
CAACAGCCTG ACTGACGATT AAAGTGCATC TGAGCCAAAG CTTGTTTCTG TGGTGGGGGT   780
GGGATCCCCT AGAACACTGC CTATGGGAAC CCTACCCACA GACTCAGAAA CGGAGGTGCC   840
CACTATAGAC AGTTGGGTGG CTTCCCTCAGG TCTTAAAGCC CCATGGGACT GAAGATGAGA   900
GGCAGGAGTG GTCCAGGGCA CCCCATACCC CTTATGATAC CCATTATACA TTTGGGACAT   960
AGTTGCCTCA AAGGAAGGTG GGCTAGACCA TTGCCTTCCT ACTACATATC CCCAGCTGCC  1020
TACAGAACTG TGACCCAGGC AACTCTGCCA TTTCAGAATT GAAGCAGGGT TCCAGCTCTA  1080
GTTGGGTTTT TCTCTTAGGG TAAACCAACC ATGGTGCCCA CTGTCAGCCT GGCACATGGT  1140
CTTCTGCAGC CAGGACAAAC ATGTCAGCAG AGGATCCTGG GAAGGGCTTC CTTAGCGTTT  1200
GAGACCAAAA TAAAATGAAG TGACTT                                     1226
```

```
        10          20          30          40
CCGTGCCGGG  CCTGCGTCGA  CTTCAAGACG  TGGATGCGGA
        50          60          70          80
CGCAGCAGAA  GCGGGACACC  AAGTTTAGGG  AGGACTGCCC
        90         100         110         120
GCCGGATCGC  GAGGAACTGG  GCCGCCACAG  CTGGGCTGTC
       130         140         150         160
CTCCACACCC  TGGCCGCCTA  CTACCCCGAC  CTGCCCACCC
       170         180         190         200
CAGAACAGCA  GCAAGACATG  GCCCAGTTCA  TACATTTATT
       210         220         230         240
TTCTAAGTTT  TACCCCTGTG  AGGAGTGTGC  TGAAGACCTA
       250         260         270         280
AGAAAAAGGT  TGTGCAGGAA  CCACCCAGAC  ACCCGCACCC
       290         300         310         320
GGGCATGCTT  CACACAGTGG  CTGTGCCACC  TGCACAATGA
       330         340         350         360
AGTGAACCGC  AAGCTGGGCA  AGCCTGACTT  CGACTGCTCA
       370         380         390         400
AAAGTGGATG  AGCGCTGGCG  CGACGGCTGG  AAGGATGGCT
       410         420         430         440
CCTGTGACTA  GAGGGTGGTC  AGCCAGAGCT  CATGGGACAG
       450         460         470         480
CTAGCCAGGC  ATGGTTGGAT  AGGGGCAGGG  CACTCATTAA
       490         500         510         520
AGTGCATCAC  AGCCAGAAAA  AAAAAAAAAA  AAAAA.....
```

5'
ATG CGG ACG CAG CAG AAG CGG GAC ACC AAG TTT AGG
Met Arg Thr Gln Gln Lys Arg Asp Thr Lys Phe Arg
         40            50            60

GAG GAC TGC CCG CCG GAT CGC GAG GAA CTG GGC CGC
Glu Asp Cys Pro Pro Asp Arg Glu Glu Leu Gly Arg
 70            80            90           100

CAC AGC TGG GCT GTC CTC CAC ACC CTG GCC GCC TAC
His Ser Trp Ala Val Leu His Thr Leu Ala Ala Tyr
        110           120           130      140

TAC CCC GAC CTG CCC ACC CCA GAA CAG CAG CAA GAC
Tyr Pro Asp Leu Pro Thr Pro Glu Gln Gln Gln Asp
       150            160           170

ATG GCC CAG TTC ATA CAT TTA TTT TCT AAG TTT TAC
Met Ala Gln Phe Ile His Leu Phe Ser Lys Phe Tyr
180           190           200           210

CCC TGT GAG GAG TGT GCT GAA GAC CTA AGA AAA AGG
Pro Cys Glu Glu Cys Ala Glu Asp Leu Arg Lys Arg
       220           230           240

FIG. 13B

```
250             260             270             280
TTG TGC AGG AAC CAC CCA GAC ACC CGC ACC CGG GCA
Leu Cys Arg Asn His Pro Asp Thr Arg Thr Arg Ala 290             300             310             320
TGC TTC ACA CAG TGG CTG TGC CAC CTG CAC AAT GAA
Cys Phe Thr Gln Trp Leu Cys His Leu His Asn Glu 330             340             350
GTG AAC CGC AAG CTG GGC AAG CCT GAC TTC GAC TGC
Val Asn Arg Lys Leu Gly Lys Pro Asp Phe Asp Cys 360             370             380             390
TCA AAA GTG GAT GAG CGC TGG CGC GAC GGC TGG AAG
Ser Lys Val Asp Glu Arg Trp Arg Asp Gly Trp Lys 400             410
GAT GGC TCC TGT GAC TAG       3'
Asp Gly Ser Cys Asp ***
```

FIG. 14

```
hALR-cDNA-AA  MRTQQKRDTKFREDCPPPDREELGRHSWAVLHTLAAYYPDL
              X:::::::  ::::::::  ::  :: ::::::::::
rALR-cDNA-AA  MRTQQKRDIKFREDCPQDREELGRNTWAFLHTLAAYYPDM
                     10        20        30        40 hALR-cDNA-AA  PTPEQQQDMAQFIHLFSKFYPCEECAEDLRKRLCRNHPDT
              ::::::::::::::  ::::::::::::  ::  :: :::
rALR-cDNA-AA  PTPEQQQDMAQFIHIFSKFYPCEECAEDIRKRIDRSQPDT
                     50        60        70        80 hALR-cDNA-AA  RTRACFTQWLCHLHNEVNRKLGKPDFDCSKVDERWRDGWK
              ::  ::  :::::::::::::::::::: ::::::::::
rALR-cDNA-AA  STRVSFSQWLCRLHNEVNRKLGKPDFDCSRVDERWRDGWK
                     90       100       110       120 hALR-cDNA-AA  DGSCD
              ::::X
rALR-cDNA-AA  DGSCD
```

FIG. 17

```
CAACATGGCG GCGCCCGGCG AGCGGGGCCG CTTCCACGGC GGGAACCTCT TCTTCCTGCC    60
GGGGGGCGCG CGCTCCGAGA TGATGGACGA CCTGGCGACC GACGCGCGGG GCCGGGGCGC   120
GGGGCGGAGA GACGCGGGCC CCTCGGCCTC GACGCCAGCC CAGGCGCCGA CCTCCGATTC   180
TCCTGTCGCC GAGGACGCCT CCCGGAGGCG GCCGTGCCGG GCCTGCGTCG ACTTCAAGAC   240
GTGGATGCGG ACGCAGCAGA AGCGGGACAC CAAGTTTAGG GAGGACTGCC CGCCGGATCG   300
CGAGGAACTG GGCCGCCACA GCTGGGCTGT CCTCCACACC CTGGCCCGCCT ACTACCCCGA   360
CCTGCCCACC CCAGAACAGC AGCAAGACAT GGCCCAGTTC ATACATTTAT TTTCTAAGTT   420
TTACCCCTGT GAGGAGTGTG CTGAAGACCT AAGAAAAAGG TTGTGCAGGA ACCACCCAGA   480
CACCCGCACC CGGGCATGCT TCACACAGTG GCTGTGCCAC CTGCACAATG AAGTGAACCG   540
CAAGCTGGGC AAGCCTGACT TCGACTGCTC AAAAGTGGAT GAGCGCTGGC GCGACGGCTG   600
GAAGGATGGC TCCTGTGACT AGAGGGTGGT CAGCCAGAGC TCATGGGACA GCTAGCCAGG   660
CATGGTTGGA TAGGGGCAGG GCACTCATTA AAGTGCATCA CAGCCAGAAA AAAAAAAAAA   720
AAAAAAA                                                            727
```

FIG. 18

```
5' ATG GCG GCG CCC GGC GAG CGG GGC CGC TTC CAC GGC GGG AAC CTC TTC
   Met Ala Ala Pro Gly Glu Arg Gly Arg Phe His Gly Gly Asn Leu Phe

TTC CTG CCG GGG GGC GCG CGC TCC GAG ATG ATG GAC GAC CTG GCG ACC
   Phe Leu Pro Gly Gly Ala Arg Ser Glu Met Met Asp Asp Leu Ala Thr

GAC GCC CCC CCC CCG GGC GCG GGG CGG AGA GAC GCG GCC GCC TCG GCC
   Asp Ala Arg Gly Arg Gly Ala Gly Arg Arg Asp Ala Ala Ala Ser Ala

TCG ACG CCA GCC CAG GCG CCG ACC TCC GAT TCT CCT GTC GCC GAG GAC
   Ser Thr Pro Ala Gln Ala Pro Thr Ser Asp Ser Pro Val Ala Glu Asp

GCC TCC CGG AGG CGG CCG TGC CGG GCC TGC GTC GAC TTC AAG ACG TGG
   Ala Ser Arg Arg Arg Pro Cys Arg Ala Cys Val Asp Phe Lys Thr Trp

ATG CGG ACG CAG CAG AAG CGG GAC ACC AAG TTT AGG GAG GAC TGC CCG
   Met Arg Thr Gln Gln Lys Arg Asp Thr Lys Phe Arg Glu Asp Cys Pro

CCG GAT CGC GAG GAA CTG GGC CGC CAC AGC TGG GCT GTC CTC CAC ACC
   Pro Asp Arg Glu Glu Leu Gly Arg His Ser Trp Ala Val Leu His Thr

CTG GCC GCC TAC TAC CCC GAC CTC CCC ACC CCA GAA CAG CAG CAA GAC
   Lau Ala Ala Tyr Tyr Pro Asp Leu Pro Thr Pro Glu Gln Gln Gln Asp

ATG GCC CAG TTC ATA CAT TTA TTT TCT AAG TTT TAC CCC TCT CAG GAG
   Met Ala Gln Phe Ile His Leu Phe Ser Lys Phe Tyr Pro Cys Glu Glu

TGT GCT GAA GAC CTA AGA AAA AGG TTG TGC AGG AAC CAC CCA GAC ACC
   Cys Ala Glu Asp Leu Arg Lys Arg Leu Cys Arg Asn His Pro Asp Thr

CGC ACC CGG GCA TGC TTC ACA CAG TGG CTG TGC CAC CTG CAC AAT GAA
   Arg Thr Arg Ala Cys Phe Thr Gln Trp Leu Cys His Leu His Asn Glu

GTG AAC CGC AAG CTG GCC AAC CCT GAC TTC GAC TGC TCA AAA GTG GAT
   Val Asn Arg Lys Leu Gly Lys Pro Asp Phe Asp Cys Ser Lys Val Asp

GAG CGC TGG CGC GAC GGC TGG AAG GAT GGC TCC TGT GAC TAG 3'
   Glu Arg Trp Arg Asp Gly Trp Lys Asp Gly Ser Cys Asp ***
```

MAMMALIAN AUGMENTER OF LIVER REGENERATION AND VARIANTS THEREOF

This is a division of application Ser. No. 08/367,968, filed Jan. 3, 1995, now U.S. Pat. No. 5,607,844, which is a Continuation-In-Part of U.S. patent application Ser. No. 08/197,496, filed Feb. 16, 1994, now U.S. Pat. No. 5,480,797, and a Continuation-In-Part of U.S. patent application Ser. No. 08/275,370, filed Jul. 15, 1994, now U.S. Pat. No. 5,550,037, the entire contents of each are hereby incorporated by reference and relied upon.

BACKGROUND OF THE INVENTION

1. Field of the Invention

This invention relates to an augmenter of liver regeneration (designated as ALR), novel polypeptides possessing a physiological activity enabling in vivo stimulation of DNA synthesis of hepatocytes, nucleic acid molecules encoding for such polypeptides, recombinant expression vectors, transformants and methods for production of such polypeptides.

2. Description of the Related Art

Stage I: ORIGINAL RESEARCH AND DEVELOPMENT OF MODELS

The involvement of the inventors in the growth factor field dates back to the discovery in 1959 that consistently successful orthotopic liver transplantation (liver replacement) in mammals was not possible without providing normal portal venous inflow from the non-hepatic splanchnic organs (1). The reason for this was-discovered in 1963 during further research to determine the optimal way to vascularize auxiliary (an extra organ as opposed to replacement) liver grafts for potential use in humans. The clinical objective was to provide a new liver without removing the diseased one, and therefore to leave the recipient with two livers.

The dog experiments evaluating this possibility (FIG. 1A) showed that the transplanted auxiliary liver allografts given portal inflow with systemic (vena caval) blood shrank to a fraction of their original size within a few days, even when there was no histopathologic evidence of immunologic rejection (2). However, this atrophy could be prevented if the allograft was nourished with normal portal venous blood, in which case the shrinkage afflicted the native liver that was deprived of this specific kind of blood (3).

The results suggested that there were pn trophic (growth sustaining) substances in portal venous blood that were largely being removed by a single passage through the first liver to which they were exposed. To establish the validity of this conclusion, non-transplant models were developed in which the animal's own liver was divided into two fragments, differing only in the kind of blood flow delivered to the right and left main portal vein branches (4,5). In essence, this created two livers in the same animal (FIGS. 1B and 1C). The sizes of the hepatocytes in the differentially perfused liver fragments were measured with a morphometric technique that correlated well with the planimetric volume determination of single cells (FIGS. 2A and 2B). The results were expressed as size units (5).

In the first of these "double liver fragment" preparations (4), one part of the liver was given high volume venous inflow from the suprarenal inferior vena cava which delivered blood to the liver from the hind quarters and trunk (FIG. 1B). The other liver portion was perfused by blood that drained in a normal way from the splanchnic organs into the portal vein. This was called "split transposition". The hepatocytes in the liver fragment vascularized with splanchnic venous blood became hypertrophic and had a 10-fold increase in basal replication. The hepatocytes in the liver portion nourished by vena caval return underwent atrophy and had only a three-fold increase in basal replication.

These changes in the fragment deprived of portal blood were indistinguishable from those caused in the whole liver by simple Eck's fistula (4–6). However, the total liver mass of the combined sides always remained the same as a normal whole liver suggesting that the size adjustments involved humorally-mediated "cross talk" between the two sides, suggestive of a growth factor or factors. Biochemical end points in the two liver fragments (5) showed that the two liver fragments apparently existed in different chemical environments that were dictated largely by the presence or absence of insulin.

Similar striking disparities between the two liver fragments were observed when the natural portal venous blood was divided between them in what became known as the splanchnic division model (FIG. 1C). Hepatocytes exposed directly to the venous effluent from the upper abdominal organs (pancreas, stomach, duodenum, and spleen) were hypertrophic (as in FIG. 2B) and hyperplastic while those in the fragment nourished by the nutrient-rich intestinal venous return developed the same kind of changes seen in conventional Eck's fistula livers (5–7).

In the most discriminating of all double liver fragment models, and the one that allowed the invention of this patent application to proceed, a completely diverting portacaval shunt (Eck's fistula) was constructed, followed by the continuous infusion of insulin or other test substances into the right or left portal vein branch (FIG. 1D). The result of this reconstructive surgery was the ability to directly compare the effect on the infused liver fragment with the non-infused side serving as a control. When insulin was given, the treated side was spared almost completely from the hepatocyte atrophy and organelle disruption characteristic of Eck's fistula (Table 1) and also exhibited the same 10-fold increase in cell renewal (Table 2) (8,9) we had attributed from previous circumstantial evidence to endogenous insulin in the split transposition and splanchnic division models.

These hypertrophic and hyperplastic effects, for which we coined the term "hepatotrophic", were not found on the untreated side, further confirming the specificity of the effect and the high degree of first pass consumption of the hormone (insulin) by the liver. This direct evidence that insulin was a growth factor completed the first stage of the discovery process leading to the present patent application.

Stage II: THE SEARCH FOR NON-INSULIN HEPATOTROPHIC FACTORS

Other Hormones—An early hypothesis stemming from the foregoing observations was that liver growth including regeneration was modulated by-the interactions of multiple hormones of splanchnic and non-splanchnic origin (5, 10–18). This trail turned cold when other hormones could not be added, in the ensuing 15 years, to the list started by insulin, except for the weakly hepatotrophic thyroxin $T_3$ (19). This intensified the search for non-hormonal growth factors. However, this search became dependent in the 1970s and 1980s on primary culture of adult rat hepatocytes as a screening bioassay (20,21), with a few notable exceptions including our continued use of the Eck's fistula in vivo model (9,19,22).

The Non-Hormonal Growth Factor—Forty years ago, Teir and Ravanti (23) and Blomqvist (24) summarized earlier work by others and reported evidence of their own that a growth stimulatory factor was present in a cell mash prepared from regenerating livers after partial hepatectomy in adult rats, and in hyperplastic weanling livers. The idea faded until 1975 when LaBreque and Pesch (25) prepared a crude cytosol from regenerating livers which augmented the normally modest regeneration response of naive (previously unaltered) rats after 34% hepatectomy when it was given intraperitoneally. We confirmed these results in canine experiments when the active cytosol was infused intraportally (26).

More importantly, the cytosol also was found to have the same hepatotrophic effects as insulin when tested with the in vivo canine Eck's fistula infusion model (22). Cytosol prepared from the livers of sham operated dogs or from the residual liver fragment of the cytosol donor one day after 70% hepatectomy was inert. However, it was hepatotrophic if the fragments were harvested two and three days post-resection at the time when hepatic regeneration in dogs is known to be maximal (27).

This "X-factor", which originally was called hepatic stimulatory substance (HSS) and more recently augmenter of liver regeneration (ALR), was not mitogenic when purified fractions were tested on cultured hepatocytes (28,29). However, throughout the steps toward its million times purification from rat liver, amino acid sequencing, and production with recombinant gene technology (this patent application), its biologic activity could be tracked by testing with the in vivo canine Eck's fistula infusion model (19,28, 29).

During the difficult Stage II development, we showed that the crude cytosol was active only if the liver of the animal injected with it already was in heightened mitosis, a condition that was present in our Eck's fistula assay in which stable heightened cell renewal is characteristic. Although we turned throughout the 1980s to the rat as a source of ALR, this in vivo assay in dogs permitted decisive identification of progressively purified fractions from rat liver.

SUMMARY OF THE INVENTION

The present invention discloses the isolation and purification of rat augmenter of liver regeneration (ALR) using both the canine in vivo Eck's fistula assay and the partially hepatectomized rodent assay.

The molecular weight of the purified rat ALR protein was determined to be 15,000 in the reduced form and 30,000 in the non-reduced form, indicating that ALR is a homodimer in its native state. Both determinations were made with SDS-PAGE.

The present invention further discloses the isolation of a full-length cDNA clone encoding a purified augmenter of liver regeneration protein prepared from the cytosol of livers from weanling rats. The full-length clone is a 1.2 kb cDNA containing an 81 bp 5'-untranslated region, a 594 bp coding region and a 551 bp 3'-untranslated region. The complete nucleotide sequence for the cDNA is given in SEQ ID NO:1. Multiple initiation sites are noted in the sequence, SEQ ID NO:1, thereby permitting at least three proteins to be encoded. The molecular weight of the ALR protein, as estimated from the deduced amino acid sequence (SEQ ID NO:2), is 15,081. This molecular weight estimate is consistent with the molecular weight estimate of the native protein determined by SDS-PAGE under reducing conditions.

The present invention further discloses the isolation of a full-length cDNA clone encoding a purified augmenter of liver regeneration protein prepared from the cytosol of human liver biopsy and of human hepatoma cell line HepG2. The full-length human cDNA clone is made up of about 727 bp containing a 615 bp coding region. The complete nucleotide sequence for the cDNA is given in SEQ ID NO:27.

The present invention also discloses the isolation and purification of human augmenter of liver regeneration, as well as three variants of human ALR, namely, ALR-V1, ALR-V2 and ALR-V3.

The molecular weight of the human ALR protein was found to be 15,028, as estimated from the deduced amino acid sequence, SEQ ID NO:23. The molecular weight of human ALR-V1 was estimated to be 23,448, the molecular weight of human ALR-V2 was estimated to be 20,834 and the molecular weight of human ALR-V3 was estimated to be 20,703 from the deduced amino acid sequences, SEQ ID NO: 29, SEQ ID NO:31 and SEQ ID NO:33, respectively, as determined from the nucleotide sequence of the full-length cDNA.

The present invention further discloses the preparation of recombinant expression vectors with exogenous DNA encoding the human or rat ALRs and the transformation of both prokaryotic and eukaryotic cell lines with the recombinant expression vectors. Such transformed cells are capable of producing recombinant ALR in culture and the recombinant ALR is of equivalent potency to the purified native ALR when tested in the canine in vivo Eck's-fistula model.

BRIEF DESCRIPTION OF THE DRAWINGS

FIGS. 1A, 1B, 1C, and 1D show liver operations which illustrate the effect of portal blood on liver growth and trophism.

FIG. 2A shows traced hepatocytes from a liver section that had a venal caval or intestinal blood supply while FIG. 2B shows traced hepatocytes from a liver section that had a splanchnic blood supply.

FIG. 5 is the deduced amino acid sequence for rat ALR. This sequence corresponds to SEQ ID NO:2.

FIGS. 6A and 6B, taken together, repesent the entire 1226 nucleotide sequence for the rat ALR cDNA. This sequence corresponds to SEQ ID NO:1.

FIG. 12 is the 515 nucleotide sequence for the human ALR cDNA. This sequence corresponds to SEQ ID NO:21.

FIGS. 13A and 13B, taken together, represent the nucleotide sequence for the 375 bp coding region of the human ALR cDNA (SEQ ID NO:22) and the deduced amino acid sequence (SEQ ID NO:23).

FIG. 14 is a comparison of the amino acid sequence of the human ALR (SEQ ID NO:23) with the amino acid sequence of the rat ALR (SEQ ID NO:2).

FIG. 17 is the 727 nucleotide sequence for the full-length human ALR cDNA. This sequence corresponds to SEQ ID NO:27.

FIG. 18 is the nucleotide sequence for the 615 bp coding region of the human ALR-V1 cDNA (SEQ ID NO:28) and the deduced amino acid sequence (SEQ ID NO:29).

DETAILED DESCRIPTION OF THE INVENTION

Figures 2A, 2B:
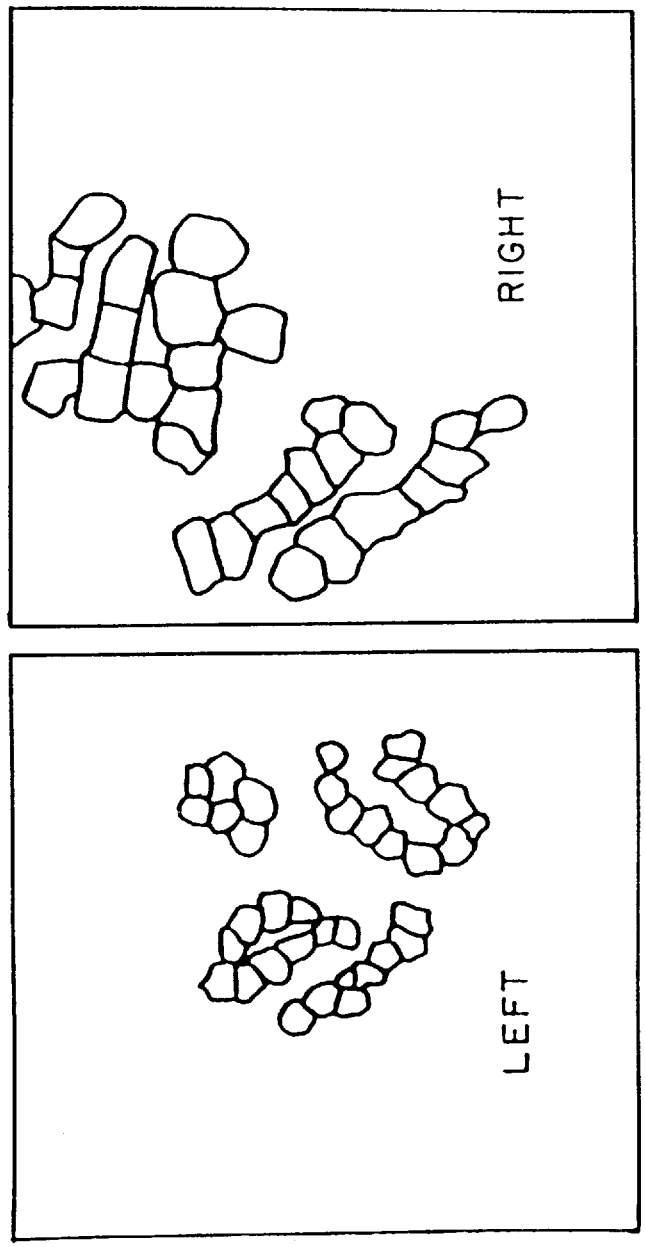
FIGS. 2A and 2B depict hepatic shadows traced during histopathological examinations cut out on standard paper and weighed as an index of hepatocyte size (5).

The substance which once was called hepatic stimulatory substance (HSS) and now referred to as augmenter of liver regeneration (ALR) was extracted from the livers of weanling rats (whose livers were hyperplastic), purified to a 30 kDa fraction using various chromatographic techniques, native SDS and reducing PAGE and immunoblotting with specific monoclonal antibody. The activity of the purified ALR was assayed at each step with the in vivo canine Eck's fistula model, also known as the dog portacaval shunt assay.

This new growth factor belongs to a physiologic family of liver growth factors of which the first identified was insulin. However, ALR has no homology to insulin or any other known growth factor.

The biochemical steps of ALR purification from the weanling rat liver are as follows:

| | Product |
|---|---|
| 1. Remove the liver, immediately after killing by guillotine, between 7:00 and 8:00 am. | |
| 2. Mince and then homogenize the liver in 150 mM sodium acetate buffer, pH 4.65 (35:100 w/v). | |
| 3. Ultracentrifuge homogenate at 24,000 xg for 30 min at 4° C. | Cytosol fraction (Cyt-F) |
| 4. Heat at 65° C. for 15 min. | |
| 5. Centrifuge at 30,000 xg for 20 min at 4° C., collect supernatant and add to it 6 vol of cold ethanol (1:6, v/v). | |
| 6. Stir at 2–8° C. for 2 hr. | |
| 7. Centrifuge at 30,000 xg for 20 min at 4° C. | |
| 8. Resuspend precipitate in 0.150 mM ammonium acetate, pH = 6. | Alcohol fraction (OH—F) |
| 9. Filter OH—F through an Amicon membrane with a molecular weight cutoff of 30,000 Da. | |
| 10. Collect the filtrate and concentrate it by a 500-Da cutoff Amicon membrane. | Mr 30,000 fraction (30 kDa-F) |
| 11. Lyophilize 30 kDa-F. | |
| 12. Resuspend lyophilized 30 kDa-F in phosphate buffer 5 mM, pH 6, and perform chromatography using mono Q HR 5/5 column with a linear 0-2000 | |

-continued

| | Product |
|---|---|
| mM NaCl gradient in phosphate buffer. | |
| 13. Collect the chromatographic peak. | 150 fraction ($F_{150}$) |

In our first experiments, the activity of each fraction was assayed in vivo with the rat or mouse 40% partial hepatectomy model, similar to the hepatectomy assays originally used by LaBreque and Pesch in rats and by us in dogs (26). Briefly, a heightened background of DNA synthetic activity in vivo was induced in host rats and mice by a 40% partial hepatectomy.

Six hours after the partial hepatectomy, rats were given i.p. injections of two ml of various extracts at protein concentrations as indicated in Table 3. Seventeen hours later, 50, $\mu$Ci [$^3$H]thymidine were injected i.p. and the animals were sacrificed one hour later.

Extracts (0.2 ml volume) were also administered i.p. to mice at 30 hours after 40% partial hepatectomy and DNA synthesis was studied 18 hours later. [$^3$H]thymidine (10 $\mu$Ci/mouse) was injected i.p. one hour before sacrifice (i.e., 47 hours following partial hepatectomy). Nonhepatectomized rats received injections of extracts 24 and 18 hours before determination of [$^3$H]thymidine incorporation, and mice received injections at 48, 24 and 18 hours. [$^3$H]thymidine incorporation, labeling and mitotic indexes were determined as previously described (22).

An augmentation of all three parameters, beyond the modest response that is usually present in 40% PH or in unoperated animals was considered to be indicative of a proliferative inducing activity of the liver extracts (29).

Table 3 shows the results expressed as augmented DNA synthesis versus the degree of purification. However, this assay was too imprecise to permit demonstration of a statistically significant effect. Further purification beyond fraction 150 was obtained through the use of nondisassociating polyacrylamide gel electrophoresis and the use of specific monoclonal antibody (28). An aliquot of 0.6 mg lyophilized fraction $F_{150}$ resuspended in Tris buffer, 0.025M, pH 8.3, underwent electrophoresis using nondisassociating PAGE (28,29) on 8% acrylamide.

With this technique, $F_{150}$ generates several distinct bands and the gel can be divided into four discrete zones from which the proteins can be eluted. The resulting eluates, acrylamide fractions 1–4 ($AcrF_1$–$F_4$), were dialyzed against 150 mM ammonium acetate, lyophilized, and stored at −70° C. until being tested further. This was the last fraction assayed by the rat hepatectomy model (Table 3).

In addition to this progress in purification, we turned to the in vivo canine Eck's fistula model as our standard assay, using the partial hepatectomy rat model only sporadically for spot checks. For the definitive assay, i.e., the Eck's fistula model, conditioned female beagle dogs weighing 8.3 to 13 kg were anesthetized with intravenous sodium pentobarbital, halothane and nitrous oxide.

Side-to-side portacaval shunt was performed and converted to a functional end-to-side shunt by ligation of the portal vein above the anastomosis (FIG. 1D). The main right and left portal veins were isolated, and the right vein was ligated. The left portal branch was cannulated with a 2.4 mm (internal diameter) cannula that was advanced for one cm, secured and led through the abdominal wall (Cormed II AIF, Cormed Inc., Murray Hill, N.J.) that was incorporated into a nonrestricting light body cast.

Test substances dissolved in saline modified by the addition of 5 mmol/L ammonium acetate and 5 mg/L BSA (to avoid aggregation on the plastic tubing) were infused continuously at 25 ml/day for 4 days beginning promptly after completion of the portacaval shunt. For positive controls, the classical insulin experiments were always repeated. For negative controls, it was established that the vehicle was inert.

The animals were given a sugar water diet ad libitum on the day of the operation and a regular diet thereafter. Before the animals were killed, hepatic and kidney function tests were obtained. Rises in serum creatinine or bilirubin or falls in serum albumin were not seen. Minor increases in serum transaminase and alkaline phosphatase typical of Eck's fistula (7) were common. All dogs were active, ate normally and appeared clinically well.

Pathological and Cytological End Points

The pathological and cytological end points measured were the same as in the previous growth factor research (8,9,19,22). Four days after portacaval shunt, 0.2 mCi/kg of intravenous [$^3$H]thymidine was given with a specific activity of 80 to 90 Ci/mmol (Dupont New England Nuclear Research Products, Boston, Mass.). Two hours later, while the dogs were under sodium pentobarbital anesthesia, specimens were taken from left and right lobes of the liver and fixed in 10% normal buffered formalin. The dogs were killed with an intravenous bolus of potassium chloride. The patency of the anastomosis and the correct position of the catheter tip were confirmed.

The liver tissue was processed and stained with hematoxylin and eosin. Autoradiography was carried out with Kodak NTB2 liquid emulsion (Eastman Kodak, Rochester, N.Y.) with an exposure time of at least 30 days. The number of replicating hepatocytes as an index of hepatocyte regeneration was determine by counting the number of [$^3$H] thymidine-labeled nuclei per 1,000 hepatocytes.

The size of individual hepatocytes (index of hypertrophy or atrophy) was determined by tracing out at least 500 midzonal liver cells projected on standard thickness paper, cutting out the individual silhouettes and weighing each (5,8,9,22). This method has been shown to be accurate for determining hepatocyte cell size and has been validated by planimetry and studies of unicellular organisms, the size of which has been determined directly (5).

In normal, unaltered dogs 1.5+0.5 (S.D.) labeled hepatocytes per 1,000 hepatocytes are present in the liver, with the size of midzonal hepatocytes being 0.16+0.01 (S.D.) size units. After Eck's fistula, the replication rate is nearly tripled (8,9,19,22), and the hepatocyte size is almost halved within four days (8,9,19,22), after which a stable state exists (6,30).

The exceptional reproducibility of these changes makes it easy to determine the effects of active growth factors on this transformation. Growth factors prevent the atrophy and increase further the already heightened cell renewal. Each experiment serves as its own control because the cell replication and size in the directly infused liver lobes can be compared with these measures in the contralateral uninfused lobes.

When acrylamide fraction 4, Acr-F$_4$, was administered as a continuous left portal vein infusion beginning six hr after portacaval shunt, the mitotic rate tripled in the left liver lobe while no effect was seen in the right side of the liver. This effect was completely eliminated with the addition of anti-Acr-F$_4$ monoclonal antibody (28) to the infusion fluid (see Table 4 for comparable results). The monoclonal antibody vehicle was inert when tested alone.

Determination of Rat ALR Amino Acid Sequences

Figure 3:
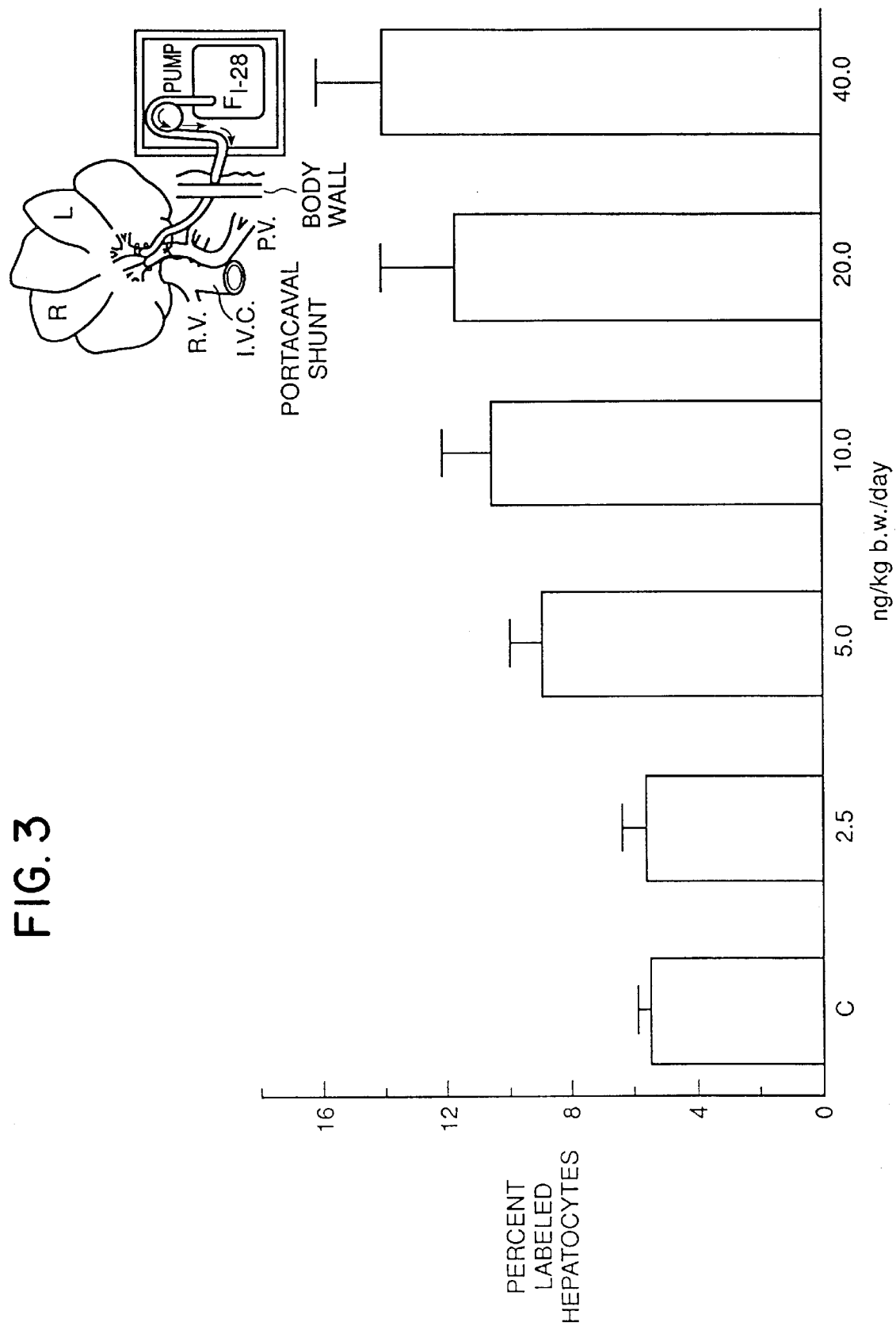
FIG. 3 demonstrates a dose-response effect on liver proliferation of the 30 kDa band infused in the left lobe of dogs with portacaval shunt (PCS).

200 μg of Acr-F$_4$ were separated by SDS PAGE. Four bands were identified and tested in the dog portacaval shunt model. The 30 kDa band was found to be active. FIG. 3 shows the activity and dose response curve for the 30 kDa band.

To determine the amino acid sequence, the gel was stained with Coomassie Brilliant Blue, and the 30 kDa band was sliced, homogenized with 150 μl of buffer (0.1M Tris-HCl [pH 9.5], 0.3% SDS) and incubated at 37° C. for 18 hr. The sample was filtered through a 0.22 μm filter (Ultrafree-C3GV, Millipore) and the filter was washed once with 100 μl of the same buffer. A total of 250 μl of 30 kDa filtrate was further purified by Phenyl-5PW RP column chromatography (4.6×75 mm TOSOH) equilibrated with 0.1% TFA (trifluoroacetic acid [V/V%]).

The 30 kDa band was eluted from the column with the solvent mixture of isopropanol and acetonitrile (1:1) containing 0.1% TFA and eluted at a concentration gradient of 40%. The peak was collected, lyophilized and combined with 200 μl of 50-mM Tris-HCl buffer (pH 9.5). The resultant solution was then incubated with 1 μg of Achromobacter liticus protease I (EC 3.4.21.50) at 37° C. for 15 hr.

The digested peptides were then eluted from an ODS chromatography column (AP-302, S-530, 4.6×150 mm YMC) which had been equilibrated with 0.1% TFA. The elution agent was a 1:1 mixture of isopropanol with acetonitrile (containing 0.1% TFA). A linear gradient was run from 0 to 80% (a 0 to 80% gradient of a 1:1 mixture of isopropanol with acetonitrile).

The amino acid sequence was determined from the N-terminus of each peak by Edman degradation with Protein Sequencer 477A and Analyzer 120 A (Applied Biosystems Co).

The following amino acid sequences were obtained:*

| | |
|---|---|
| ALR-19 | Phe-Tyr-Pro-Xaa-Glu-Glu-Xaa-Ala-Glu-Asp-Ile (SEQ ID NO:4) |
| ALR-20 | Leu-Gly-Lys-Pro-Asp-Phe-Asp-Xaa-Ser-Xaa-Val (SEQ ID NO:5) |
| ALR-26 | Xaa-Ile-Asp-Arg-Ser-Gln-Pro-Asp-Thr-Ser-Thr-Arg-Val-Ser-Phe-Xaa-Gln-Xaa-Leu-Xaa-Xaa-Leu (SEQ ID NO:6) |

All three sequences have no homology with known sequences in the Protein Identification Resource (PIR) R34.0 data bank as of September 1992.

*At this point, the "Xaa" amino acids had not yet been identified. These have been identified subsequently (see SEQ ID NO:2).

Isolation of Rat cDNA Clones

A) Isolation of mRNA

Total cellular RNA was isolated from the livers of two week old Fischer rats using the guanidine isothiocyanate procedure of Chomczynski et al. (31). Three mg of RNA were isolated from one gram of liver and then resuspended in 500 μl elution buffer (10 mM Tris-HCl, [pH 7.5], 1 mM EDTA, 0.1% SDS) and mixed with 500 μl of Oligotex-dT30 (Japan Roche Company). The mixture was heated for 5 minutes at 65° C. and then chilled on ice. 1/10 volume of 5M NaCl was added and incubated for 5 minutes at 370° C. MRNA was precipitated with Oligotex after spinning for 5 minutes at 10,000 xg. Elution buffer was added to the precipitate and the solution was vortexed and heated for 5 minutes at 65° C. mRNA was recovered in the supernatant after spinning for 5 minutes at 10,000 xg. The above procedure yielded about 15 μg of mRNA.

B) Preparation of cDNA Library cDNA was prepared from 5 μg mRNA obtained by procedure (A) using the cDNA synthesis system (Amersham) and ligated into a λ-gt11 vector with EcoRI adapters and packaged using the cDNA cloning system (Amersham). In all, approximately 1×10$_9$ recombinant phages were generated.

C) screening of cDNA Library

The rat ALR cDNA was isolated in three stages. First, single-stranded cDNA prepared from two week old rat livers was amplified by PCR with degenerated oligonucleotide primers based on the partial amino acid sequence. Next, the PCR product was sequenced to confirm the primer sequence in the insert (32). Finally, PCR product was used to screen the cDNA library.

C-1 Single Stranded cDNA Synthesis

Single-stranded cDNA was synthesized from liver mRNA primed with the oligodeoxynucleotide, 5'-AACTGGAAGAATTCGCGGCCGCAGGAA(T$_{18}$)-3' (SEQ ID NO:7) which is complementary to the poly(A) tail of mRNA and includes a Not I restriction site, using first strand cDNA synthesis kit (Pharmacia).

C-2) PCR

Single-stranded cDNA was amplified by PCR with a mixture of 5' primers:

---
5'-ATIGA(T/C)CGIAG(T/C)CA(A/G)CCIGA(T/C)AC-3' (SEQ ID NO:8),
5'-ATIGA(T/C)CGITCICA(A/G)CCIGA(T/C)AC-3' (SEQ ID NO:9),
5'-ATIGA(T/C)AG(A/G)AG(T/C)CA(A/G)CCIGA(T/C)AC-3' (SEQ ID NO:10) and
5'-ATIGA(T/C)AG(A/G)TCICA(A/G)CCIGA(T/C)AC-3' (SEQ ID NO:11),
---

(wherein I is inosine).

These primers include sequences of all possible codons specifying amino acid sequence Ile-Asp-Arg-Ser-Gln-Pro-Asp-Thr of ALR 26 (SEQ ID NO:12) and 3' primer, 5'-GCCGCAGGAA(T)$_{10}$-3' (SEQ ID NO:13) with 4 mM of each primer in 80 mM KCl, 1.5 mM MgCl$_2$, 10 mM Tris-HCl (pH 8.8), 500 μg/ml BSA, 0.1% sodium cholate, 0.1% Triton X-100, 200 μM deoxynucleotide triphosphate (dNTP), and 1 unit of Tth DNA polymerase (Toyobo) in 100 μl of reaction mixture. The PCR was performed under the following conditions: 95° C. for 1 minute, 58° C. for 28 minutes, 75° C. for 3 minutes per cycle for 40 cycles. The PCR products were analyzed by agarose gel (1.2%). A 360 bp fragment was isolated from a gel, subcloned in EcoRV sites of pBluescript by TA cloning (33) and sequenced by the dideoxy method (32) with Sequenase (United States Biochemical Company). Insert fragment cloned in pBluescript was cut with SalI and XbaI, separated and extracted from the gel. PC-ALR 26–24 subclone was selected for screening for the cDNA library.

C-3) cDNA Screening by Plaque Hybridization

The hybridization was performed by standard procedure (34).

The PCR probe obtained (C-2) was labelled with (α-$^{32}$P) dCTP by the multiprimed DNA labelling system (Amersham). After hybridization, the filters were withdrawn from the solution, washed with 0.9M NaCl/0.09M sodium citrate at 65° C. four times. The filters were air-dried and autoradiographed at 70° C. for one day on an X-ray film using the intensifying screen. After developing the film, the plaques corresponding to the signal region were scraped off from the master plate. The above procedure was repeated to purify the plaques having a positive signal. Four positive clones were eventually isolated.

D) Structural Analysis of the cDNA Clone

Figure 4:
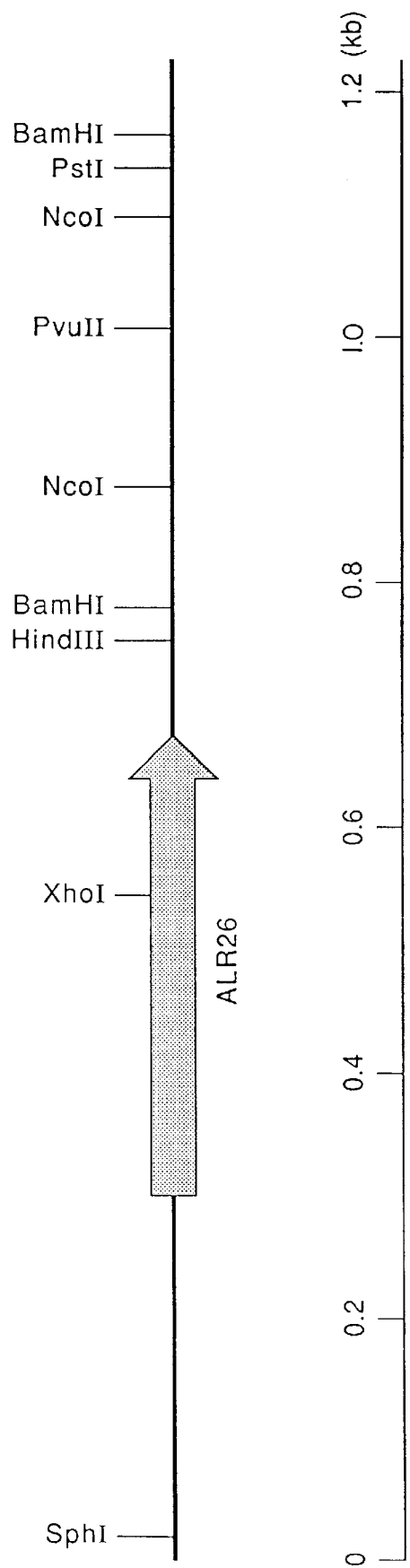
FIG. 4 is a schematic representation of the rat ALR cDNA showing the location of various restriction sites.

ALR-26-5 cDNA was digested with EcoRI and ligated in pBluescript. The resultant plasmid was further analyzed by restriction enzyme digestion and sequencing. As seen in FIG. 4 and SEQ ID NO:1, rat ALR cDNA is about 1.2 kb (1226 bp) in entire length. When the cDNA of ALR 26-5 was searched for the longest open reading frame, an open reading frame, which starts at the translation initiation codon (ATG) at nt 82–84 and ends at the termination signal (TAA) at nt 676–678, was found. A second ATG codon was found at nt 160–162 and a third ATG codon at nt 301–303. FIG. 5 shows the deduced amino acid sequence (SEQ ID NO:2) of the coding sequence starting at the third ATG codon (SEQ ID NO:3 and FIGS. 6A and 6B). The region corresponding to the amino acid sequences of the peptides derived from ALR-19, ALR-20, and ALR-26 are underlined and this indicates that the cDNA of ALR-26-5 is the cDNA coding for rat ALR protein. These results show that the coding size is 594 nucleotides long and codes for three proteins with estimated molecular weights of 15,081, 20,193 and 22,835. The estimated molecular weight by SDS-PAGE of the purified native ALR from the liver of a weanling rat was 30 kDa under non-reducing conditions and 15 kDa under the reducing conditions.

It is presumed that the native form of ALR is a homodimer. Also ALR does not contain an N-linked glycosylation site. ALR is a novel protein. In Gene Bank R74.0, as of December 1992, ALR's only homology (50%) is with yeast nuclear gene ERV1, which is involved in oxidative phosphorylation and vegetative growth and is essential for yeast life (35).

Preparation of Recombinant Rat ALR by COS Cells, E. col, and S.cerevisiae

A. Construction of COS cell expression vector CDMmcs-dALR26

Figure 7:
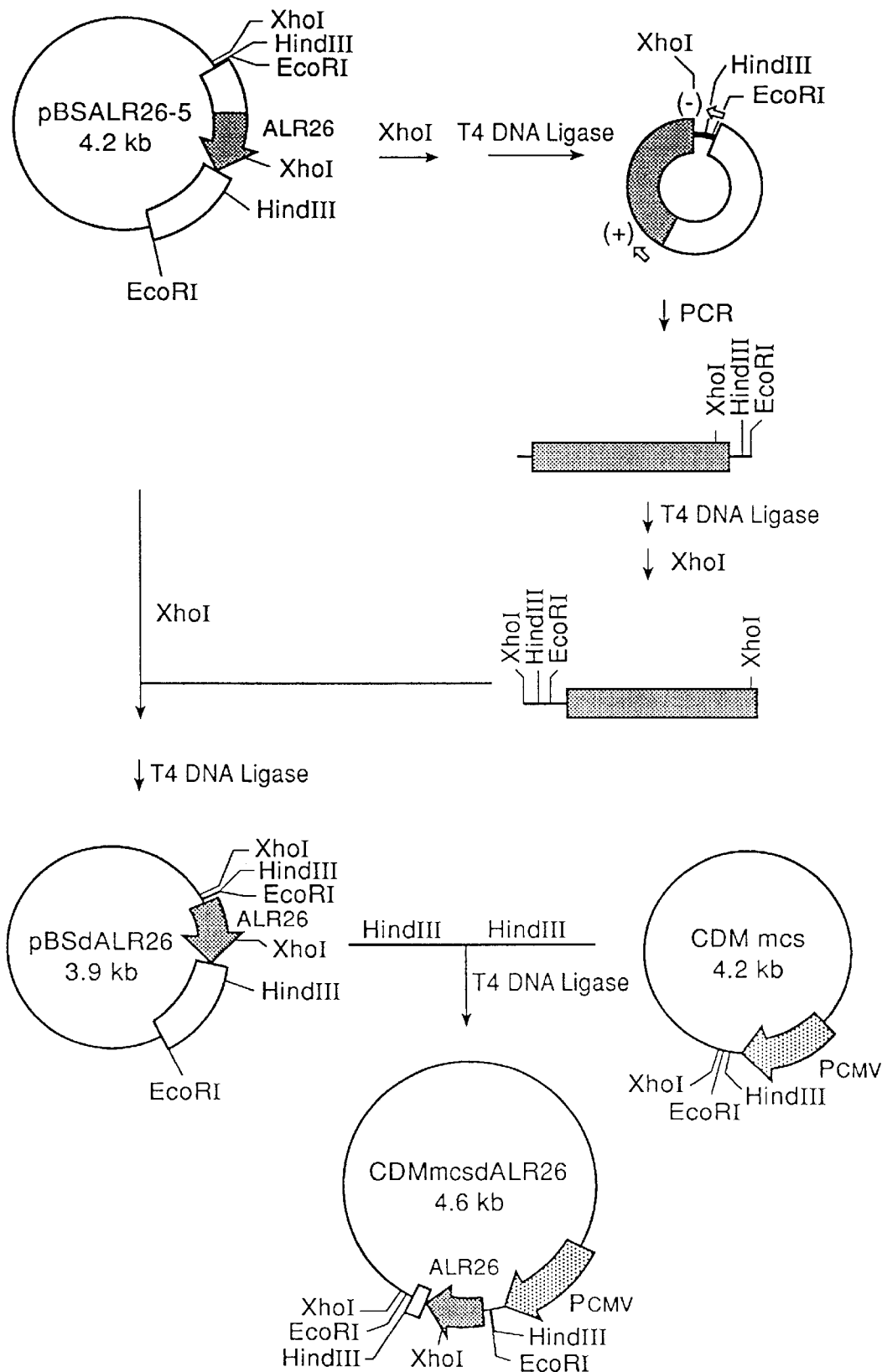
FIG. 7 is a schematic representation of the preparation of vector CDMmcsdALR26 used to infect COS-1 cells.

To express the cloned cDNA ALR26-5 in COS cells and ensure the ALR activity, an expression vector was constructed as follows. The highly G-C rich region of the ALR cDNA was eliminated by the PCR-based in vitro mutagenesis technique (42). The 1.2 kb EcoRI DNA fragment of the phage clone ALR26-5 was inserted into the EcoRI site of pBluescript SK+ (Stratagene). The plasmid DNA of the subclone designated as pBSALR26-5 was digested with XhoI and self-ligated with T4 DNA ligase and then used as the template for the PCR. This step was necessary to shorten the length of the cDNA to be amplified. PCR was carried out using the thermostable Pfu DNA polymerase (Stratagene) and synthetic primers 5'-TGGACTTCAAGTCGTGGATG-3' (SEQ ID NO:14) and 5'-GAATTCGATATCAAGCTTATCG-3' (SEQ ID NO:15) which were based on the nucleotide sequences around the translation initiation codon at nt 301–303 of ALR26-5 and the multiple cloning site of pBluescript SK+, respectively. The PCR product was self-ligated, digested with XhoI and then used to replace the XhoI fragment of pBSALR26-5, generating plasmid pBSdALR26. The expression vector CDMmcs (36) is a derivative of CDM (37) whose HindIII-XbaI fragment which included the stuffer sequence of the cloning sites has been replaced with the HindIII-XbaI multiple cloning site of Rc/RSC (Invitrogen). The 0.5 kb HindIII fragment of pBSdALR26 was inserted into the HindIII site of CDMmcs which is located downstream of the cytomegalovirus promoter. The expression vector CDMmcs-dALR26 was finally obtained (FIG. 7) and used to transfect the COS cells.

COS-1 cells (ATCC CRL-1650) were transfected with CDMmcsdALR26 by the DEAE-dextran method (38) and tested for the production of r-ALR by the following procedure. COS-1 cells were first suspended to a concentration of about $1\times10^6$ cells/ml in DMEM (Nissui Co.) with 10% FCS. Two ml of the suspension were placed into each well of a 60 mm dish and incubated overnight at 37° C. in a $CO_2$ incubator.

Subsequently, the medium was removed and the cells were washed with DMEM twice. Two ml of DMEM containing 50 mM Tris-HCl (pH 7.4) and 400 μg/ml DEAE-dextran (Pharmacia) containing two μg of CDMmcsdALR26 were added to the cells and the mixture was allowed to stand in a $CO_2$ incubator for 12 hr. The media was removed from the cells and the cells were washed with DMEM (without FCS) twice. Two ml of DMEM (without FCS) was added to the plate and incubated.

After two days, the culture media were separated and the cells were scraped from the plate, homogenized in new DMEM (without FCS), and then centrifuged at 1600 xg for five minutes to get the cytosolic fraction. Both the culture medium and cytosolic fraction were assayed for in vivo thymidine uptake activity in hepatocytes in the dog porta-caval shunt assay. The results are shown in Table 4. ALR activity was observed only in the cytosolic fraction.

B. Construction of E. coli Expression Vector pKKdALR26

Figure 8:
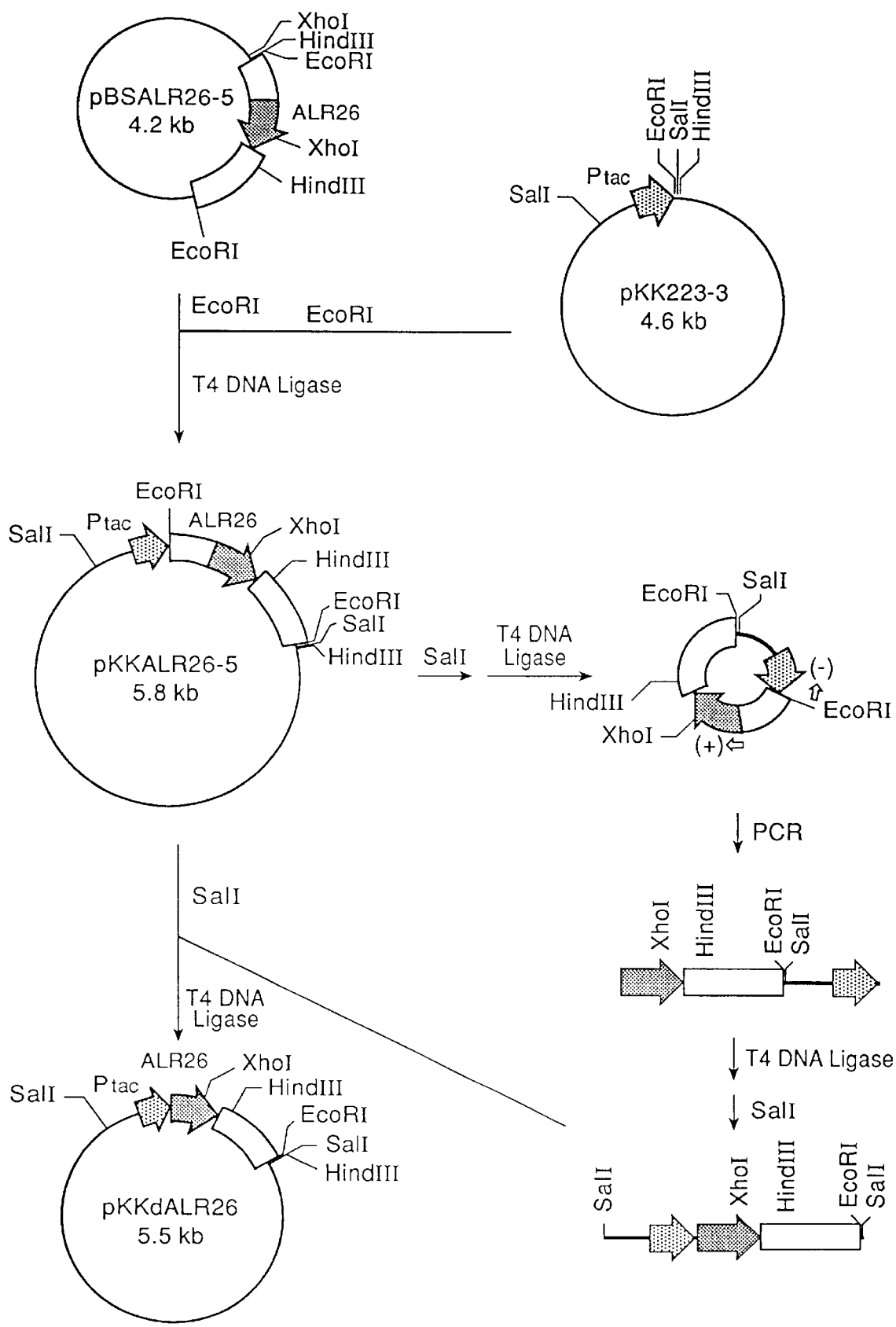
FIG. 8 is a schematic representation of the preparation of plasmid pKKALR26 used to express ALR cDNA in E. coli.

To express the cloned cDNA ALR26-5 in E. coli cells and obtain the gene product, an expression vector was constructed as follows. The protein coding sequence of the ALR26-5 cDNA was inserted just downstream of the translational initiation signal of the expression vector pKK223-3 (Pharmacia) using the PCR based in vitro mutagenesis technique as described for COS, the mammalian expression vector (see Section A, above). The EcoRI fragment of ALR26-5 cDNA was inserted into the EcoRI site which is located downstream of the tac promoter and ribosome-binding site, then generating the plasmid pKKALR26-5. The plasmid DNA of pKKALR26-5 was digested with SalI and then self-ligated to provide the template for the PCR. PCR was carried out with Pfu DNA polymerase (Stratagene) and synthetic primers 5'-ATGCGGACCCAGCAGAAG-3' (SEQ ID NO:16) and 5'-ATTCTGTTTTCCTGTGTGAAATT-3' (SEQ ID NO:17) which were based on the nucleotide sequences around the translational initiation codon at nt 301–303 of ALR26-5 and the transcription/translation regulatory region of pKK223-3, respectively. The PCR was self-ligated and digested with SalI, then used to replace the SalI fragment of pKKALR26-5. The resulting plasmid pKKdALR26 (FIG. 8) was used to express the ALR cDNA in E. coli.

E. coli JM109 cells were transfected with E. coli expression plasmid pKKdALR26 obtained above by the standard $CaCl_2$-phosphate-transformation method. The transformant was inoculated in five ml LB and incubated overnight. 500 μl of the culture was inoculated in 50 ml LB medium for 2.5 hr. One mg IPTG (isopropyl-D-thiogalactopyranoside, Sigma) was added to the culture and incubated another six hours. The cells were precipitated by centrifugation at 3,000 xg for 10 minutes. Cells were resuspended in five ml of 10 mM PBS (pH 7.0) and five mg/ml lysozyme (Sigma) was added and the suspension was incubated for 30 minutes at room temperature. After incubation, the suspension was sonicated for two minutes at full scale. The sonicated cell suspension was centrifuged at 7,000 xg for 15 minutes. The supernatant was subsequently applied on a Mono Q ion exchange column and eluted with a linear 0-300 mM NaCl gradient. The 150 mM NaCl eluate was collected and passed through an Affi-Prep Polymixin Matrix column (Bio Rad) to remove endotoxin from the sample. Using the dog porta-caval shunt model, the biological activity of the E. coli derived ALR was also confirmed.

C. Construction of S. cerevisiae Expression Vector pYEU (A-ALR26)

To express the cloned cDNA ALR26-5 in Saccharomyces cerevisiae cells and obtain the gene product in the culture medium, an expression vector was constructed as follows. The protein coding sequence of the ALR26-5 cDNA was inserted just downstream of the polyhistidine sequence and a specific five amino acid cleavage site by enterokinase (DDDDK; SEQ ID NO:26) (expression vector pRSET-A, Invitrogen) for the single-step purification by immobilized metal affinity chromatography using the PCR-based in vitro mutagenesis technique as described above in Section A for the COS mammalian expression vector. Upstream of this fragment the signal sequence of wheat alpha-amylase was inserted for secretion, and then a generated fragment was inserted downstream of the gal promoter in the expression vector pYEUra3 (Clontech).

Figure 9:
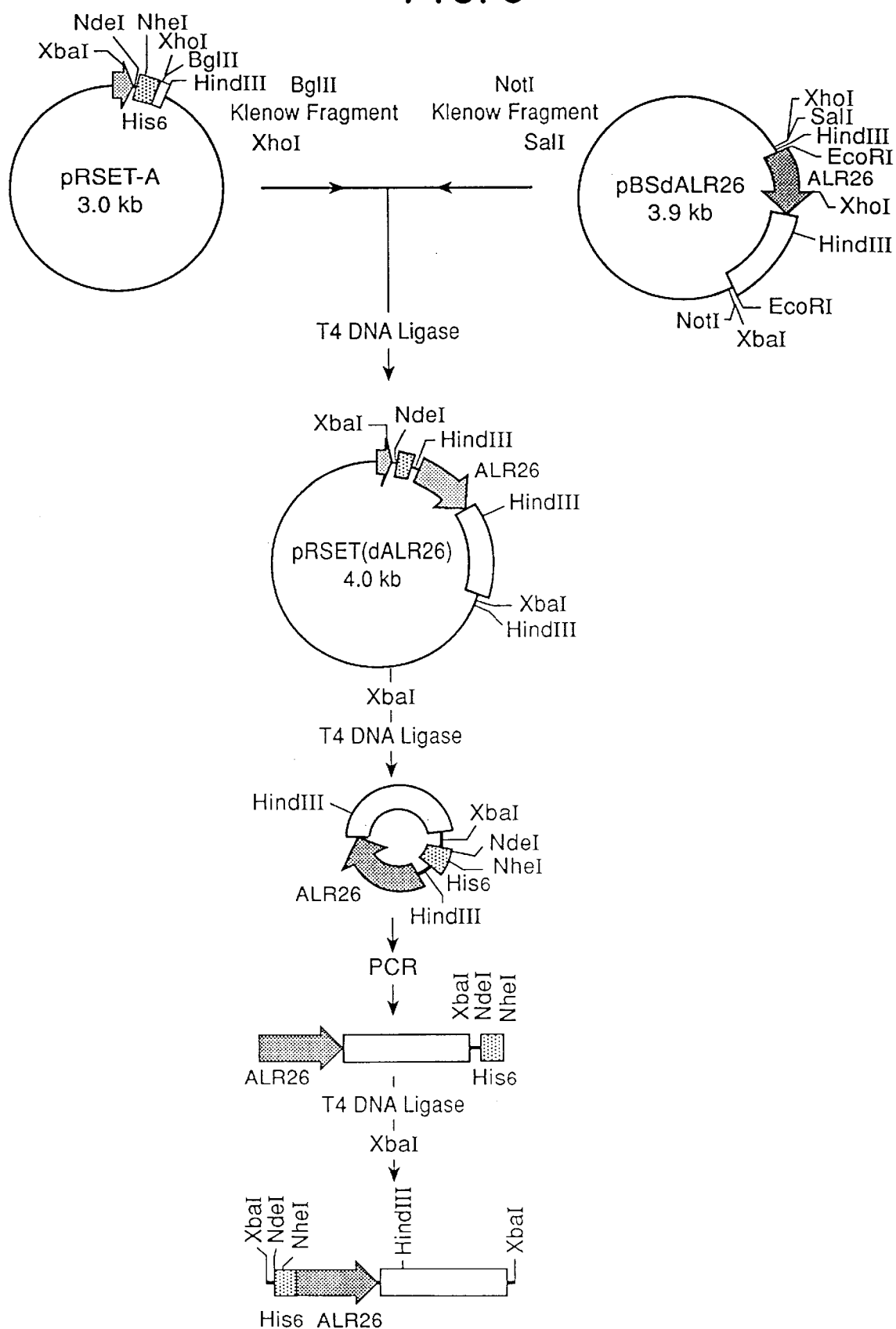
FIG. 9 is a schematic representation of the preparation of plasmid pRSET(dALR26) and the polyhistidine sequence—ALR cDNA sequence used in the preparation of piasmid pYEU(A-ALR26).

The SalI and blunt/ended NotI fragment of ALR26-5 cDNA was inserted into XhoI and blunt/ended BglII site which is located downstream of the polyhistidine and enterokinase cleavage site (FIG. 9). Then, plasmid pRSET (dALR26) was digested with XbaI, and self-ligated to generate the template for the PCR procedure.

The PCR procedure was performed with Pfu DNA polymerase (Stratagene) and synthetic primers 5'-ATGCGGACCCAGCAGAAG-3' (SEQ ID NO:16) and 5'-CTTATCGTCATCGTCGTACA-3' (SEQ ID NO:18) which were based on the nucleotide sequence around the translational initiation site at nt 301–303 of the ALR26-5 and the enterokinase cleavage site of pRSET-A, respectively.

The PCR product was self-ligated and digested with XbaI, then ligated to the XbaI site of the pBluescript SK+; and the plasmid pBS (His6-ALR26) was obtained. The complementary synthetic nucleotides of wheat alpha-amylase signal sequence, 5'-GATCATGCGAACAAACACTTGTCCCTC-TCCCTCTTCC TCGTCCTCCTTGGCCTGTCGGCCAG-CTTGGCCTCCGG-3' (SEQ ID NO:19) and 5'-CCGGAGGCCAAGCTGGCCGACAGGCCAAGGAG-GAC GAGGAAGAGGGAGAGGGACAAGTGTTTGTT-CGCCAT-3' (SEQ ID NO:20) were synthesized.

Figure 10:
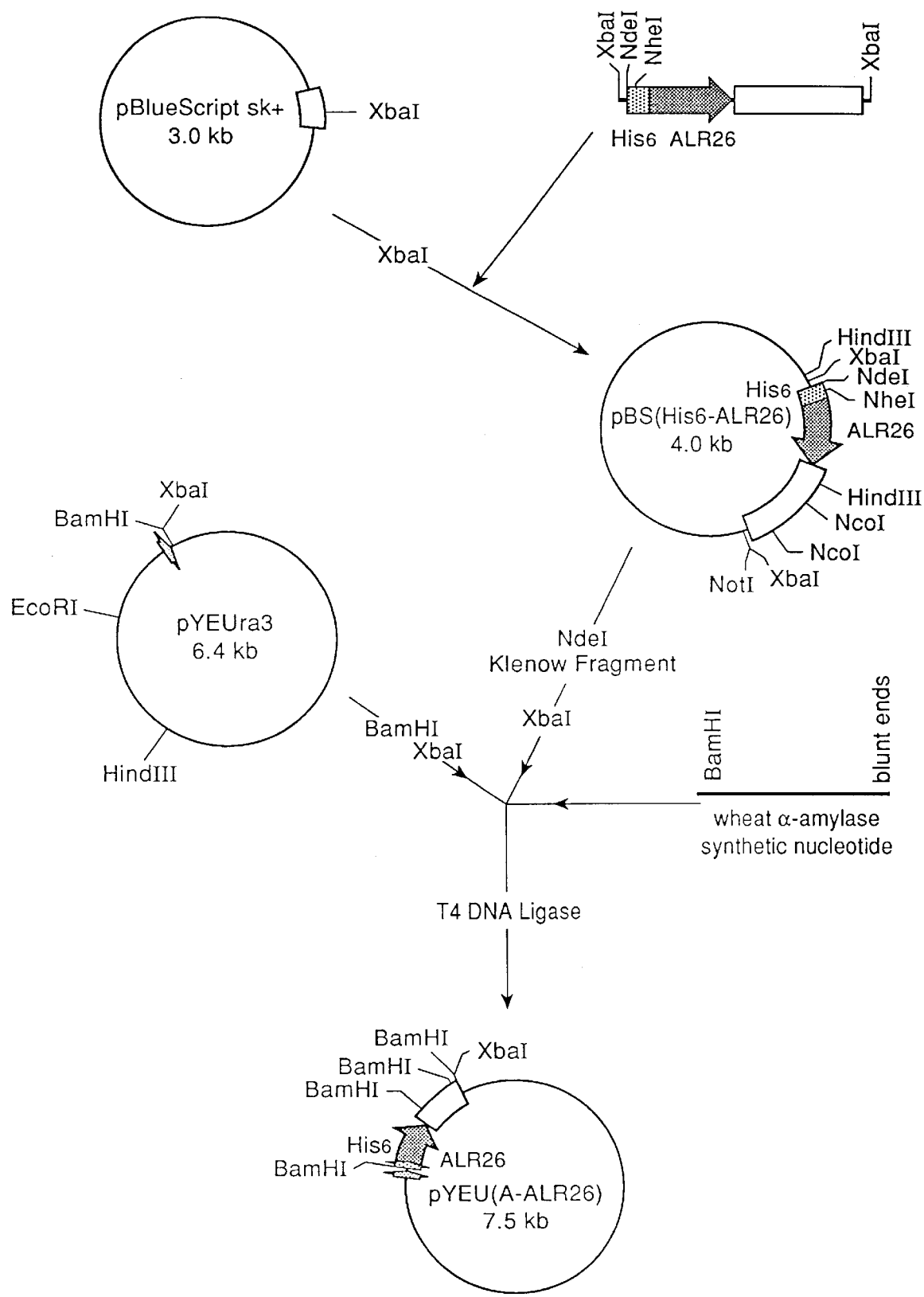
FIG. 10 is a schematic representation of the preparation of plasmid pYEU(A-ALR26) used to express ALR cDNA in S. cerevisiae.

The signal sequence generated by annealing of the above two fragments was ligated in BamHI and XbaI sites of the pYEUra3 together with the XbaI and blunt/ended NdeI fragment of plasmid pBS(His6-ALR26). The resulting plasmid pYEU(A-ALR26), FIG. 10, was used to express the ALR cDNA in S. cerevisiae.

S. cerevisiae DBY747 cells (Yeast Genetic Stock Center, Berkeley, Calif.) were transformed according to the method of Hinnen (39) with expression vector PYEU (A-ALR26) obtained above. The transformant was inoculated in five ml YEPD medium (5% yeast extract, 2% peptone and 2% glucose) and incubated overnight. 500 μl of the culture was inoculated in 50 ml YEPD medium for eight hours.

The culture medium was collected by centrifugation, adjusted to 500 mM NaCl and pH 8.0 with $KPO_4$, loaded onto a two ml ProBond metal affinity column (Invitrogen) pre-equilibrated with a buffer (40 mM $KPO_4$, pH 8.0, 500 mM NaCl) and washed four times in the same buffer. ALR was eluted with four ml of elution buffer (40 mM $KPO_4$, pH 4.0, 500 mM NaCl) and was concentrated by centrifugation on a 10,000 MW cutoff Centricon-lo (Amicon).

The protein was treated with two µg of enterokinase in a buffer (10 mM Tris pH 8.0, 10 mM KPO₄). Using the dog portacaval shunt model, the biological activity of *S. cerevisiae* derived ALR was confirmed.

D. In Vivo Testing of Recombinant Rat ALR

As mentioned above, after the ALR expression vector was transfected into COS-1 cells, the cells were cultured and proteins harvested from both the culture supernatant and the cytosolic fraction from the COS cell homogenate. Both samples were tested for ALR activity in the Eck's fistula model (Table 4). A dose-dependent stimulation of DNA synthesis was detected in the cytosolic fraction but not in the culture supernatant. This activity was abolished by the anti-ALR monoclonal antibody (Table 4).

Similar results were obtained when the *E. coli* or the *S. cerevisiae* derived recombinant ALR was assayed in the dog portacaval shunt model.

Isolation of Human cDNA Clones

A) Materials

The human hepatoma cell line (HepG2) cDNA library was purchased from Clontech. Human Liver biopsy was obtained from the Department of Surgery at the University of Pittsburgh School of Medicine. Enzymes for DNA manipulation were obtained from Toyobo. Radioisotope was purchased from Amersham.

B) Synthesis of Oligonucleotides

Oligonucleotides encoding 5' of the coding region (5'-ATGCGGACGCAGCAGAAGCGGGACA-3'; SEQ ID NO:24) and 3' of the coding region (5'-CTAGTCACAGGAGCCATCCTTCC-3'; SEQ ID NO:25) of the human ALR cDNA for PCR were synthesized on the Applied Biosystems 381A DNA synthesizer.

C) Extraction of Total RNA

Total RNA was extracted from the human hepatoma cell line HepG2 and the human liver biopsy sample by the guanidine isothiocyanate procedure of Chomczynski et al. (31), as described above in Section A) of the Isolation of Rat cDNA Clones.

D) PCR

Single-stranded cDNA was synthesized from RNAs primed with oligo-d(T) using a first strand synthesis kit (Pharmacia). Then PCR was performed under the following condition: 95° C. for 1 min, 52° C. for 25 min and 75° C. for 3 min per cycle for 40 cycles using Tth DNA polymerase (Toyobo) with the above primers. The PCR products were analyzed on agarose gel and the band was extracted from a gel and subcloned into Eco RV site of pBluescript by TA-cloning (33) for the nucleotide sequencing (32).

E) Isolation of cDNA Clone

For cDNA cloning of the human ALR homologue of rat ALR, human hepatoma cell line, HepG2 cDNA library (Clontech) was screened with the rat ALR cDNA as a probe (1.2 kb EcoRI fragment; SEQ ID NO:1) which was labelled with α-p³² dCTP by the multiprimed DNA labelling system (Amersham). The hybridization was performed by standard procedure (34) except that the hybridization and the washing were done at 52° C. (34).

Figure 11:
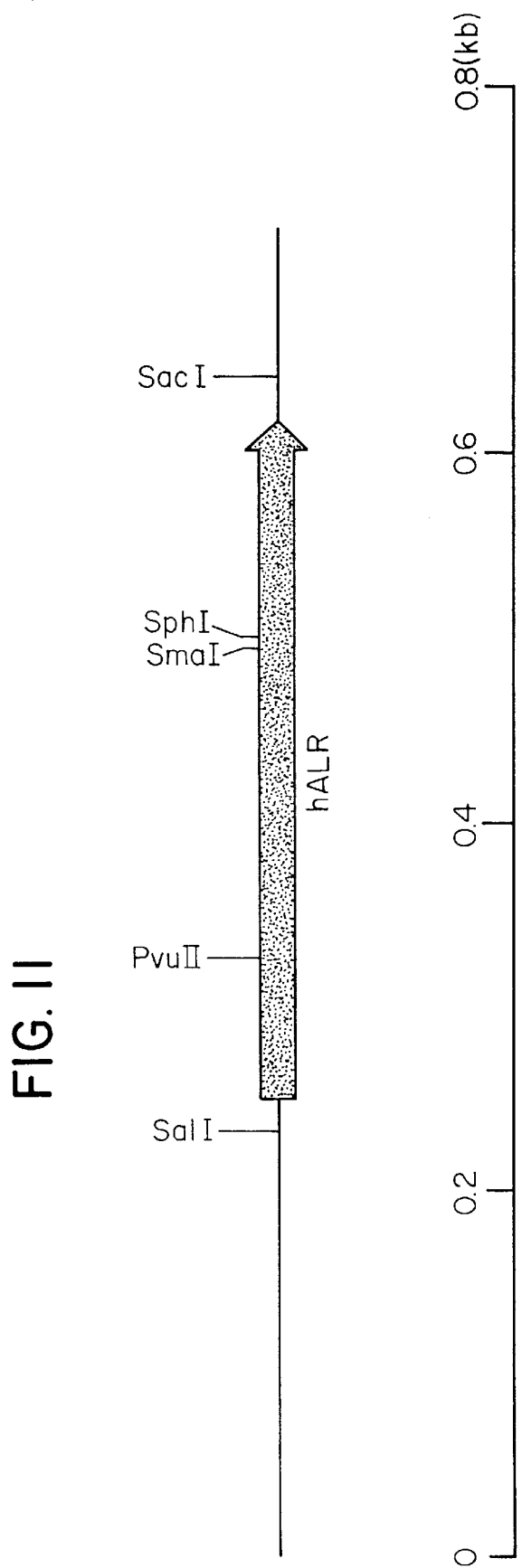
FIG. 11 is a schematic representation of the human ALR cDNA showing the location of various restriction sites.

Two positive clones were obtained from 2×10 clones. They were subcloned into pBluescript or M13 and were further analyzed by restriction enzyme mapping (FIG. 11) and sequencing (FIG. 12). As seen in FIG. 12, human ALR cDNA is about 515 bp in entire length. When the cDNA of human ALR was searched for the longest open reading frame, the translation initiation codon (ATG) of human ALR was presumed to start at nucleotide (nt) 34–36 and terminate (TAG) at nt 409–411. The entire coding region consists of 375 bp (SEQ ID NO:22) which correspond to the 375 bp coding region of the rat ALR cDNA (SEQ ID NO:3). This sequence (SEQ ID NO:22) was also confirmed in the sequence of cDNA from normal human liver.

Thus, the 0.5 kb human ALR cDNA consists of a 33 bp 5'-untranslated region, a 375 bp coding region and a 107 bp 3'-untranslated region (SEQ ID NO:21).

FIGS. 13A and 13B (SEQ ID NO:23) show the deduced amino acid sequence from the human cDNA sequence. A comparison of the sequences from the human ALR with those of the rat ALR shows 71% homology at the nucleotide level and 86% homology at the amino acid level (FIG. 14).

Figure 15:
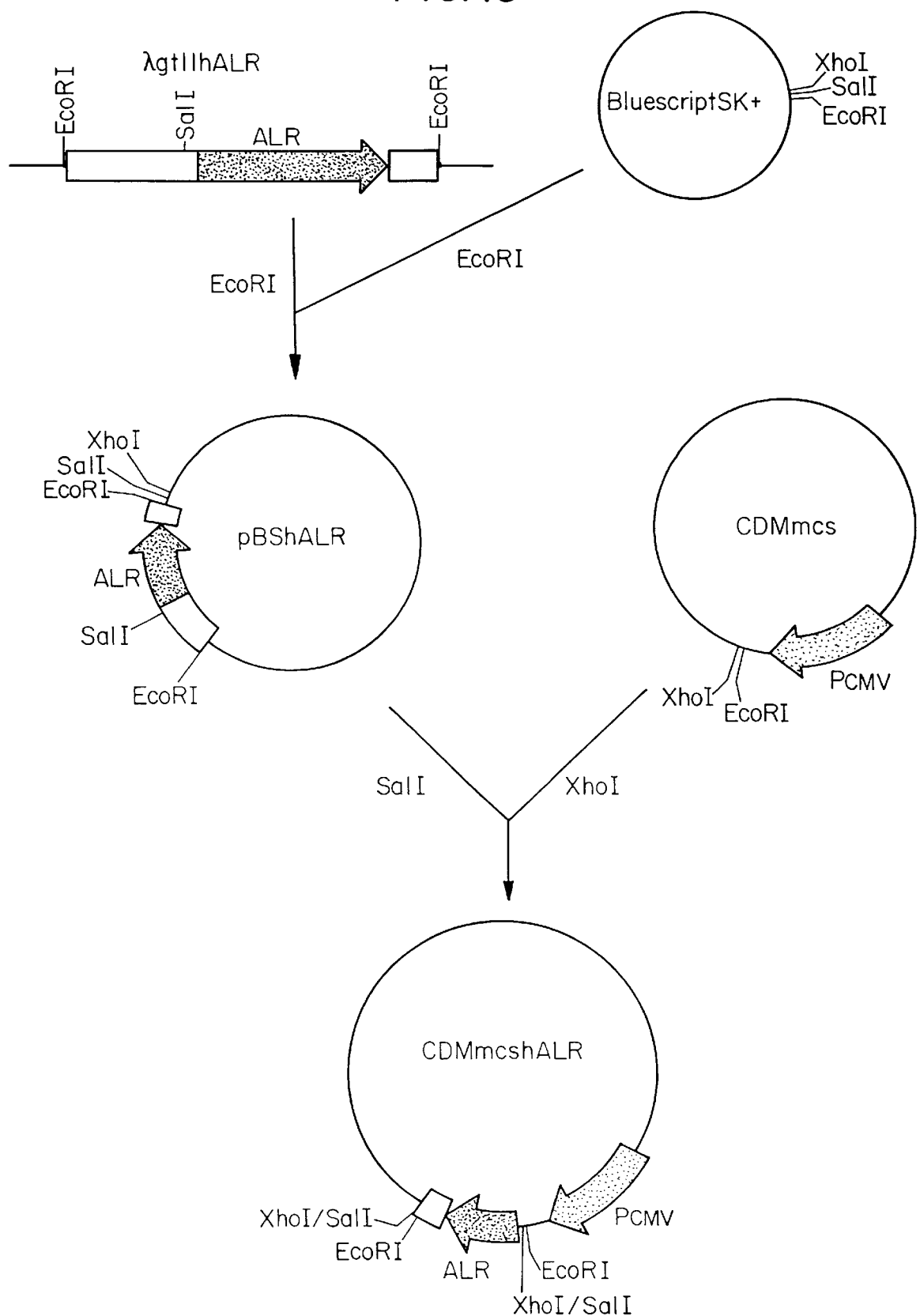
FIG. 15 is a schematic representation of the preparation of vector CDMmcshALR used to transfect COS-1 cells.

Construction of Expression Vector CDMmcshALR and Production of Recombinant hALR in COS Cells In order to express the cloned cDNA and ensure the activity of the human ALR, an expression vector was constructed as follows. The 0.75 kb EcoRI fragment of the λgtll hALR clone was inserted into the ECORI site of pbluescript SK+ (pBShALR). The 0.5 kb SalI fragment containing the human ALR coding region from pBShALR was ligated into the XhoI site of CDMmcs which is located downstream of the cytomegalovirus promoter. The expression vector CDMmcshALR was obtained (FIG. 15).

The expression vector CDMmcshALR was then used to transfect COS cells, which produced recombinant human ALR. The procedures employed were the same as those described above for the construction of COS cells expressing rALR, except that the expression vector CDMmcshALR was used instead of expression vector CDMmcsdALR26. Other cells useful for the expression of CDMmcshALR include CHO and C127I (also known as C127).

Isolation of Full-Length. Human ALR cDNA

Figure 16:
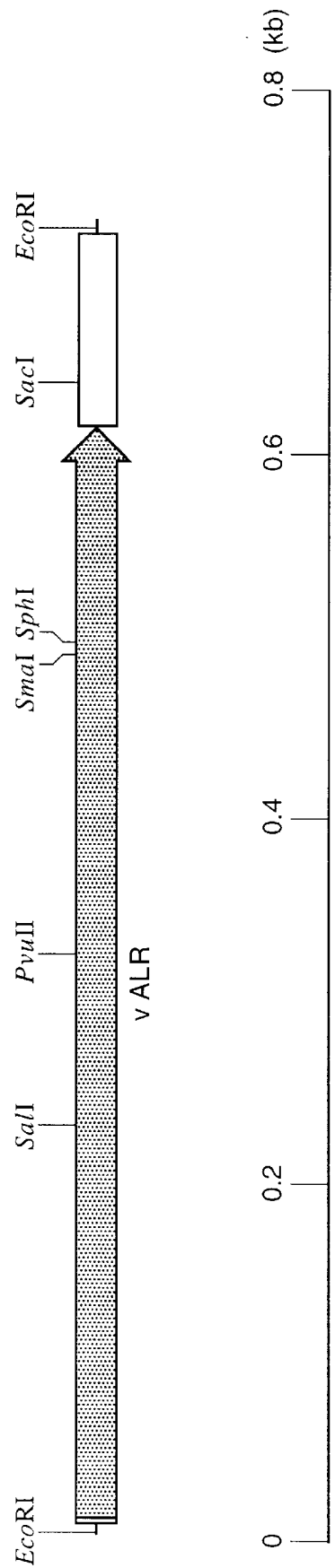
FIG. 16 is a schematic representation of the full-length human ATR cDNA encoding all of the ALR variants and showing the location of various restriction sites.

Two positive clones obtained as the cDNA coding for human ALR homologue of rat ALR were further analyzed by restriction enzyme mapping (FIG. 16) and sequencing (FIG. 17). As seen in FIG. 17, this cDNA is about 727 bp in entire length (SEQ ID NO:27). When this cDNA was searched for the longest open reading frame, an open reading frame, which starts at the translation initiation codon (ATG) at nt 5–7 and ends at the termination signal (TAG) at nt 620–622, was found. A second ATG codon was found at nt 80–82, a third ATG codon at nt 83–85 and a fourth ATG codon at nt 245–247.

The entire coding region consists of 615 bp (SEQ ID NO:28). FIG. 18 (SEQ ID NO:29) shows the deduced amino acid sequence of the entire coding region of 615 bp. The amino acid sequence comprises a protein of 205 amino acids with a calculated molecular weight of 23,448. This ALR protein is referred to as human ALR-V1.

The coding region starting at the second ATG codon consists of 540 nt (SEQ ID NO:30) and encodes a protein of 180 amino acids (SEQ ID NO: 31) with an estimated molecular weight of 20,834. This ALR protein is referred to as human ALR-V2.

The coding region starting at the third ATG codon consists of 537 nt (SEQ ID NO:32) and encodes a protein of 179 amino acids (SEQ ID NO: 33) with an estimated molecular weight of 20,703. This ALR protein is referred to as human ALR-V3.

The coding region starting at the fourth ATG codon consists of 375 nt (SEQ ID NO:22) and encodes a protein of 125 amino acids (SEQ ID NO:23) with an estimated molecular weight of 15,028. This ALR is referred to as human ALR.

Thus, the 0.72 kb human cDNA consists of a 4 bp 5'-untranslated region, a 615 bp coding region and a 108 bp 3'-untranslated region, including the termination codon TAG and the poly (A) region (SEQ ID NO:27). The 615 bp coding region encodes four proteins, human ALR-V3, ALR-V2, ALR-V1 and ALR.

Since the native rat ALR protein is believed to consist of 125 amino acids, the human ALR protein consisting of 125 amino acids was designated human ALR. Accordingly, the other human ALR proteins were designated ALR V-1 (Variant 1), ALR V-2 (Variant 2) and ALR V-3 (Variant 3).

Figure 19:
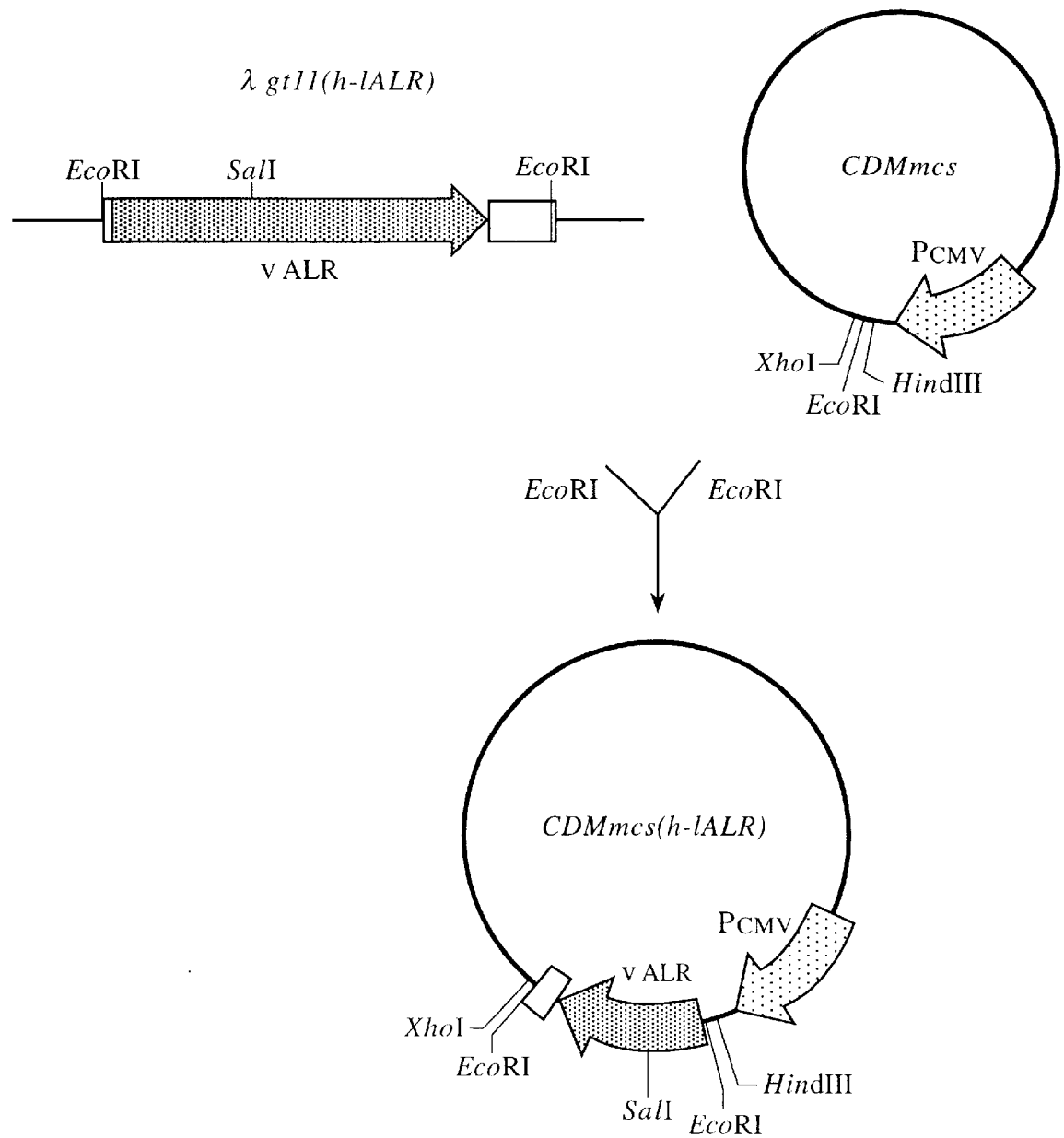
FIG. 19 is a schematic representation of the preparation of vector CDMmcs(h-1ALR) used to transfect COS-1 cells.

Construction of Expression Vector CDMmcs(h-1ALR) and Production of Recombinant Human Variant ALR in COS Cells In order to express the cDNA with an open reading frame of 615 nucleotides long encoding the ALR, ALR-V1, ALR-V2 and ALR-V3 proteins, an expression vector was constructed as follows. The 0.75 kb EcoRI fragment of the λgt11 hALR clone was inserted into the EcoRI site of CDM which is located downstream of the cytomegalovirus promoter. The expression vector CDMmcs(h-1ALR) was obtained (FIG. 19).

The expression vector CDMmcs(h-1ALR) was then used to transfect COS cells. The procedures employed were the same as those described above for the construction of COS cells expressing rALR, except that the expression vector CDMmcs(h-1ALR) was used instead of expression vector CDMmcsdALR26. Other cells useful for the expression of CDMmcs(h-1ALR) include CHO and C127I (also known as C127).

A sample of the cytosolic fraction from the COS cell homogenate was tested for ALR activity in the Eck's fistula model (Table 5). A stimulation of DNA synthesis was detected in the cytosolic fraction from the cells transfected with the expression vector CDMmcs(h-1ALR).

Multiple initiation sites are noted in the human cDNA (see SEQ ID NO:27), thereby permitting at least four proteins to be encoded. Western blot analysis using anti-ALR antibody of a sample of the cytosolic fraction from the COS cell homogenate transfected with the expression vector CDMmcs(h-1ALR) showed that the homogenate contained at least three protein bands with a molecular weight of about 24,000, 23,000 and 21,000 in the reduced form.

It is further noted that in many expression systems, especially mammalian host cell systems, the primary amino acid sequence translated is often modified by post-translational processings such as glycosylation or the cleaving off of a signal sequence.

POTENTIAL SCIENTIFIC AND THERAPEUTIC APPLICATIONS OF ALR

The number of growth factors with demonstrable in vivo hepatotrophic activity (see Table 2) is small. Unlike all of the other putative hepatotrophic substances, the augmenter of liver regeneration (ALR) is the product of regeneration, not something that has been used to cause it. An intriguing question has been what is the nature of ALR. Now that the ALR gene and recombinant molecule are available (this patent application), this question is susceptible to analysis, as well as the physiologic significance of the protein. We expect an immediate linkage with experimental oncology, research on aging, and the interphase between immunology and growth control.

The most obvious immediate clinical implication for any new liver specific growth factor is its use for the treatment of hepatic failure, eg., hepatocirrhosis—to promote the regeneration upon which clinical recovery depends (40,41). With currently available growth factors, this has been an unfulfilled fantasy, not only because there are so few of these substances, but because they can only initiate, not govern and perpetuate regeneration. Whether ALR can go beyond this therapeutically will have to be determined by direct experimentation and then clinical trial.

The governance of regeneration once begun, including its perpetuation and control, has not been understood but has been postulated to be by two broad mechanisms. One is directly biochemical involving interlocking phosphorylation-dephosphorylation pathways with protein kinase (tyrosine, serine, threonine) way stations connecting cell surface receptors to the nucleus and ultimately gene expression products from the nucleus. The other is immunologic whereby these gene products control the major histocompatibility complex (MHC) gene products and alter MHC Class II expression of non-parenchymal cells of the liver which ultimately control hepatocyte proliferation through an interactive cytokine/growth factor network. With recombinant AUR and development of molecular probes, such receptor-reactor networks can now be systematically examined.

Similarly, pathologic growth (cancer) will be susceptible to analysis in the field of oncology. Of great interest will be the determination of anti-ALR effects of specific monoclonal antibodies which now can be raised with the recombinant ALR. Also, the availability of the gene will permit the prompt creation of transgenic animals, and study of the physiologic effect of the new gene in these animals.

Another use for ALR will be to create a liver environment in which genes can be transfected. Gene transfection and subsequent genetic therapy require a transfection environment characterized by heightened cellular proliferation (43). As discussed above in the "Description of the Related Art", such an environment can be created in the liver by partial hepatectomy. With the present invention, a pharmacologic approach with ALR can now be used to induce an in vivo hyperplastic microenvironment conducive to transfection of genes. In addition to ALR, other hepatic growth factors, such as tri-iodothyronine ($T_3$), can be used to induce liver hyperplasia (44). Obviously, $T_3$ and other hepatic growth factors (19) can be used in combination with ALR in order to create the requisite in vivo hyperplastic microenvironment for gene transfection.

Finally, we have emphasized throughout this patent application the interspecies nature of ALR, exemplified by the retention of full potency of rat ALR in the phylogenetically distant dog which allowed us to develop an interspecies assay system (The Eck's fistula model). As shown above, human ALR is highly or greater homologous with rat ALR.

The extension of this patent application to the human gene will have a conventional purpose. Although the rat ALR can be used for clinical purposes (most sera or anti-lymphocyte globulins and even commercial insulin are heterologous proteins), slight interspecies differences in the amino acid sequence of a protein can cause immune reactions, often limiting the duration of treatment with a given protein. The human ALR will avoid this kind of complication.

REFERENCES

The following publications were cited above and are incorporated herein by reference:

1. Starzl T E, Kaupp H A Jr, Brock D R, Lazarus R E, Johnson R V: Reconstructive problems in canine liver homotransplantation with special reference to the postoperative role of hepatic venous flow. Surg Gynecol Obstet 111:733–743, 1960.

2. Starzl T E, Marchioro T L, Rowlands D T Jr, Kirkpatrick C H, Wilson W E C, Rifkind D, Waddell W R: Immunosuppression after experimental and clinical homotransplantation of the liver. Ann Surg 160:411–439, 1964.

3. Marchioro T L, Porter K A, Dickinson T C, Faris T D, Starzl T E: Physiologic requirements for auxiliary liver homotransplantation. Surg Gynecol Obstet 121:17–31, 1965.

4. Marchioro T L, Porter K A, Brown B I, Otte J-B, Starzl T E: The effect of partial portacaval transposition on the canine liver~ Surgery 61:723-732, 1967.

5. Starzl T E, Francavilla A, Halgrimson C G, Francavilla F R, Porter K A, Brown T H, Putnam C W: The origin, hormonal nature, and action of hepatotrophic substances in portal venous blood. Surg Gynecol Obstet 137:179–199, 1973.

6. Starzl T E, Porter K A, Kashiwagi N, Lee I Y, Russell W J I, Putnam C W: The effect of diabetes mellitus on portal blood hepatotrophic factors in dogs. Surg Gynecol Obstet 140:549–562, 1975.

7. Starzl T E, Porter, K A, Francavilla A: The Eck fistula in animals and humans. Curr Probl Surg 20:687-752, 1983.

8. Starzl T E, Porter K A, Putnam C W: Intraportal insulin protects from the liver injury of portacaval shunt in dogs. Lancet 2:1241–1246, 1975.

9. Starzl T E, Watanabe K, Porter K A, Putnam C W: Effects of insulin, glucagon, and insulin/glucagon infusions on liver morphology and cell division after complete portacaval shunt in dogs. Lancet l(No.7964):821–825, 1976.

10. Leffert H L: Growth control of differentiated fetal rat hepatocytes in primary monolayer culture—VII, hormonal control of DNA synthesis and its possible significance to the problem of liver regeneration. J Cell Biol 62:792, 1974.

11. Leffert H, Alexander N M, Faloona G, Rubalcava B, Unger R: Specific endocrine and hormonal receptor changes associated with liver regeneration in adult rats. Proc Natl Acad Sci USA 72:4033–4036, 1975.

12. Honey R W: Control of growth of mammalian cells in cell culture. Nature 258:487–490, 1975.

13. Bucher N L R, Swaffield M N: Regulation of hepatic regeneration in rats by synergistic action of insulin and glucagon. Proc Natl Acad Sci USA 72:1157–1160, 1975.

14. Whittemore A D, Kasuya M, Voorhees A B Jr, Price J B Jr: Hepatic regeneration in the absence of portal viscera. Surgery 77:419, 1975.

15. Duguay L R, Orloff M J: Regulation of liver regeneration by the pancreas in dogs. Surg Forum 27:355–357, 1976.

16. MacManus J P, Franks W, Youdale T, Braceland B M: Increases in rat liver cyclic AMP concentrations prior to the initiation of DNA synthesis following partial hepatectomy or hormone infusion. Biochem Biophys Res Commun 49(5) :12071–1207, 1972.

17. Thrower S, Ord M G: Hormonal control of liver regeneration. Biochem J 144:361–369, 1974.

18. Byus C V, Hedge G A, Russell D H: The involvement of cyclic AMP dependent protein kinase(s) in the induction of ornithine decarboxylase in the regenerating rat liver and in the adrenal gland after unilateral adrenalectomy. Biochim Biophys Acta 498(1):39–45, 1977.

19. Francavilla A, Starzl T E, Porter K, Scotti-Foglieni C, Michalopoulos G K, Carrieri G, Trejo J, Azzarone A, Barone M, Zeng Q: Screening for candidate hepatic growth factors by selective portal infusion after canine eck fistula. Hepatology 14:665–670, 1991.

20. Michalopoulos G, Cianciulli H D, Novotny A R, et al: Liver regeneration studies with rat hepatocytes in primary culture. Cancer Res 42:4673–4682, 1982.

21. Nakamura T, Nawa K, Ichihara A: Partial purification and characterization of hepatocyte growth factor from serum of hepatectomized rats. Biochem Biophys Res Commun 122:1450–1459, 1984.

22. Starzl T E, Jones A F, Terblanche J. Usui S, Porter K A, Mazzoni G: Growth-stimulating factor in regenerating canine liver. Lancet 1:127–130, 1979.

23. Teir H, Ravanti K: Mitotic activity and growth factors in the liver of the whole rat. Exp Cell Res 5:500–507, 1953.

24. Blomqvist K: Growth stimulation in the liver and tumor development following intraperitoneal injections of liver homogenates in the rat. Act a Pathol Microbiol Scand 121(Suppl)121, 1957.

25. LaBrecque D R, Pesch L A: Preparation and partial characterization of hepatic regenerative stimulator substance (SS) from rat liver. J Physiol 248:273–284, 1975.

26. Terblanche J, Porter K A, Starzl T E, Moore J, Patzelt L, Hayashida N: Stimulation of hepatic regeneration after partial hepatectomy by infusion of a cytosol extract from regeneration dog liver. Surg Gynecol Obstet 151:538–544, 1980.

27. Francavilla A, Porter K A, Benichou J, Jones A F, Starzl T E: Liver regeneration in dogs: Morphologic and chemical changes. J Surg Res 25:409–419, 1978.

28. Francavilla A, Barone M, Van Thiel D H, Mazzaferro V, Prelich J, Starzl T E: Further steps of HSS (hepatic stimulatory substance) purification. Dig Dis Sci 36(5):674–680, 1991.

29. Francavilla A, Ove P, Polimeno L, Coetzee M, Makowka L, Rose J, Van Thiel D H, Starzl T E: Extraction and partial purification of hepatic stimulatory substance in rats, mice and dogs. Cancer Res 47:5600–5605, 1987.

30. Starzl T E, Lee I Y, Porter K A, Putnam C W: The influence of portal blood upon lipid metabolism in normal and diabetic dogs and baboons. Surg Gynecol Obstet 140:381–396, 1975.

31. Chomczynski P, Sacchi N: Single step method of RNA isolation by acid guanidinium thiocyanate-phenolchloroform extraction. Anal Biochem 162(1):156–159, 1987.

32. Sanger F, Nicklen S, Coulson A R: DNA sequencing with chain terminating inhibitors. Proc Natl Acad Sci USA 74(12):5463–5467, 1977.

33. Marchuk D, Drumm M, Saulino A, Collins F S: Construction of Tvectors, a rapid and general system for direct cloning of unmodified PCR products. Nucl Acids Res 19(5):1154, 1991.

34. Maniatis T, Fritsch E F, Sambroak J: Molecular cloning; A laboratory manual (Cold Spring Harbor Lab, Cold Spring Harbor, N.Y.), 1982.

35. Lisowsky T: Dual function of a new nuclear gene for oxidative phosphorylation and vegetative growth in yeast. Mol Gen Genet 232:58–64, 1992.

36. Matsumoto K, Takehara T, Inoue H, Hagiya M, Shimizu S, Nakamura T: Deletion of kringle doming or the N-terminal hairpin structure in hepatocyte growth factor results in marked decreases in related biological activities. Biochem Biophys Res Comm 181(2):691–699, 199 1

37. Seed B: An LFA-3 cDNA encodes a phospholipid-linked membrane protein homologous to its receptor CD2. Nature 329(6142):840–842, 1987.

38. Yokota T, Lee F, Rennick D, Hall C, Arai N, Mossmann T, Nabel G, Canter H, Arai K: Isolation and characterization of a mouse cDNA clone that express mast-cell growth-factor activity in monkey cell. Proc Natl Acad Sci USA 81:1070–1074, 1984.

39. Hinnen A, Hicks J B, Fink G R: Transformation of yeast. Proc Natl Acad Sci USA 75(4):1929–1933, 1978.

40. Lee W M: Acute liver failure. New Eng J Med 329:1862–1872, 1993.

41. Francavilla A, DiLeo A, Polimeno L, Gavaler J, Pellicci R, Todo S, Kam I, Prelich J, Makowka L, Starzl T E: The effect of hepatic stimulatory substance, isolated from regenerating hepatic cytosol, and 50,000 and 300,000 sub-fractions in enhancing survival in experimental acute hepatic failure in rats treated with D-Galactosamine. Hepatology 6(6):1346–1351, 1986.

42. PCR Protocols—A Guide to Methods and Application, Innis et al. editors, Academic Press, New York, 1990.

43. Wu G Y, Wilson J M, Shalaby F, Grossman M, Shafritz D A, Wu C H: Receptor-mediated gene delivery in vivo. Partial correction of genetic analbuminemia in Nagase rats. J Biol Chem 266: 14338–42, 1991.

44. Francavilla A, Carr B I, Azzarone A, Polimeno L, Wang Z, Van Thiel D H, Subbottin V, Prelich J, Starzl T E: Hepatocyte proliferation and gene expression induced by tri-iodothyronine ($T_3$) in-vivo and in vitro. Hepatology, in press, 1994.

TABLE 1

HEPATOTROPHIC EFFECTS OF INSULIN (WITH OR WITHOUT GLUCAGON): 4-DAY ECK FISTULA EXPERIMENT

|  | Labelled Left | Hepatocytes/1000 Right | Cell Size Left | Units Right |
|---|---|---|---|---|
| Normal Liver | 1.5 | 1.5 | .17 | .17 |
| Saline and Eck Fistula | 4.5 | 4.5 | .09 | .09 |
| Insulin (0.43/kg/d) | 16.0 | 5.0 | .17 | .09 |
| Insulin (0.16u/kg/d) | 15.0 | 5.0 | .17 | .09 |
| Glucagon (0.6 mg/kg/d) | 4.5 | 4.5 | .09 | .09 |
| Glucagon (0.005 mg/kg/d) | 4.5 | 4.5 | .09 | .09 |
| 2:1 Insulin/Glucagon | 16.0 | 4.5 | .17 | .09 |
| 2:100 Insulin/Glucagon | 15.0 | 4.5 | .11 | .07 |

*Insulin protection maintained for duration of insulin supply (at least 60 days).

TABLE 2

GROWTH FACTORS REHEALED BY ECK FISTULA (1993)

|  | REFERENCE |
|---|---|
| STIMULATORY |  |
| HORMONES: |  |
| INSULIN | 1, 3, 10 |
| GROWTH FACTORS: |  |
| CYTOSOL (AND ALR) | 4, 5 |

TABLE 2-continued

GROWTH FACTORS REHEALED BY ECK FISTULA (1993)

|  | REFERENCE |
|---|---|
| IGF II | 19 |
| TGF-ALPHA* | 19 |
| HGF* | 19 |
| IMMUNOSUPPRESSANTS: |  |
| CYCLOSPORINE | 19 |
| FK 506 | 19 |
| IMMUNOPHILINS: |  |
| FKBP12 |  |
| INHIBITORY |  |
| GROWTH FACTORS: |  |
| TGF-β** | 19 |
| IMMUNOSUPPRESSION: |  |
| RAPAMYCIN** | 19 |

*MITOGENIC IN TISSUE CULTURE
**INHIBITORY IN TISSUE CULTURE

TABLE 3

Steps of Purification and Biological Activity of ALR from Weanling Rat Liver Tested in Rat with 40% Partial Hepatectomy

| MATERIAL INJECTED | PROTEIN (μG/RAT) | DNA SYNTHESIS (CPM/MG DNA) | PURIFICATION-FOLD |
|---|---|---|---|
| Cytosol | $7.5 \times 10^4$ | 43,350 ± 8,820 |  |

TABLE 3-continued

Steps of Purification and Biological Activity of ALR from Weanling Rat Liver Tested in Rat with 40% Partial Hepatectomy

| MATERIAL INJECTED | PROTEIN (μG/RAT) | DNA SYNTHESIS (CPM/MG DNA) | PURIFICATION-FOLD |
|---|---|---|---|
| OH—F | $1.0 \times 10^4$ | 66,350 ± 11,350 | 15 |
| 30 kDa-F | $0.27 \times 10^4$ | 63,520 ± 13,220 | 52 |
| $F_{150}$ | 3 | 54,380 ± 10,200 | 38,100 |
| P—$F_{150}$ | 1 | 53,280 ± 7,900 | 110,000 |
| Acr-$F_4$ | $3 \times 10^{-1}$ | 49,350 ± 7,084 | 330,000 |

TABLE 4

EFFECT ON LIVER REGENERATION OF RECOMBINANT ALR INFUSED INTO LEFT LOBE OF PORTACAVAL DOGS WITH AND WITHOUT MONOCLONAL ANTIBODY

| Sample | Number of labelled hepatocytes per 1000 hepatocytes | |
|---|---|---|
| | L Lobe | R Lobe |
| Vector supernatant to left | 3.8 | 4.0 |
| Vector cytosol to left | 6.3 | 5.4 |
| ALR supernatant: 40 ng/kg to left | 6.4 | 6.6 |
| ALR cytosol: 20 ng/kg to left | | |
| ALR cytosol: 20 ng/kg + anti-ALR mAB to right | 10.1 | 5.1 |
| ALR cytosol: 40 ng/kg to left | 15.2 | 4.8 |

TABLE 5

EFFECT ON LIVER REGENERATION OF HUMAN ALR AND ALR VARIANT-1 INFUSED INTO LEFT LOBE OF PORTACAVAL SHUNT DOGS

| SAMPLES | NUMBER OF LABELLED HEPATOCYTES PER 1000 HEPATOCYTES | |
|---|---|---|
| | L LOBE | R LOBE |
| VECTOR CYTOSOL TO LEFT | 3.9 | 4.1 |
| h ALR CYTOSOL TO LEFT | 8.8 | 3.9 |
| h-1ALR CYTOSOL TO LEFT | 11.5 | 3.7 |

---

What is claimed is:

1. An isolated and purified protein which is a human augmenter of liver regeneration, said protein having the property of specifically stimulating the growth of liver cells.

2. The protein of claim 1, which is further characterized by being purified from human liver.

3. The protein of claim 1, whose activity can be detected in dog portacaval shunt, partially hepatectomized rat and partially hepatectomized mouse assays.

4. The protein of claim 1, which is further characterized by having a molecular weight selected from the group consisting of about 15,000, about 21,000, about 23,000 and about 24,000, as determined by SDS-PAGE under reducing conditions.

5. The protein of claim 1, which is further characterized by having an amino acid sequence selected from the group consisting of SEQ ID NO:29, SEQ ID NO:31, SEQ ID NO:33 and SEQ ID NO:23.

6. The protein of claim 1, which is further characterized by having the amino acid sequence described in SEQ ID NO:23.

7. A composition comprising a therapeutically effective amount of augmenter of liver regeneration of claim 1.

8. A therapeutic agent for hepatocirrhosis comprising the protein of claim 1.

9. An isolated and purified protein which is a human augmenter of liver regeneration, said protein comprising an amino acid sequence selected from the group consisting of SEQ ID NO:23, SEQ ID NO:29, SEQ ID NO:31 and SEQ ID NO:33.

10. An isolated and purified protein which is a human augmenter of liver regeneration produced by the process of a) cultivating a transformant harboring an expression vector containing an exogenous DNA sequence capable of expressing said augmenter of liver regeneration and b) harvesting said augmenter of liver regeneration from culture;

wherein said human augmenter of liver regeneration has an amino acid sequence selected from the group consisting of SEQ ID NO:29, SEQ ID NO:31, SEQ ID NO:33 and SEQ ID NO:23.

11. An isolated and purified protein which is a human augmenter of liver regeneration produced by the process of a) cultivating a transformant harboring an expression vector containing an exogenous DNA sequence capable of expressing said augmenter of liver regeneration and b) harvesting said augmenter of liver regeneration from culture;

wherein said DNA sequence is selected from the group consisting of SEQ ID NO:27, SEQ ID NO:28, SEQ ID NO:30, SEQ ID NO:32 and SEQ ID NO:22.

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 1226 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
CGCGCGCTGG  CGGTGGCATG  CGCGCTGCTC  TGTCCCGTCT  CCTGCACGCC  CTCTTGGCCC    60
CGCTGCTCGT  ACGCCAGCAA  TATGGCGGCG  CCCAGCGAAC  CCGCAGGTTT  CCCTCGCGGC   120
AGTCGCTTCT  CCTTCCTGCC  GGGCGGCGCG  CACTCGGAGA  TGACCGACGA  CCTGGTGACT   180
GACGCGCGGG  GCCGCGGCGC  AAGGCATAGA  AAAGACAACG  CCCCTGCCGC  GGCCCCGGCG   240
CCGAAAGGTT  TGGAGCACGG  GAAGCGACCG  TGCCGGGCCT  GCGTGGACTT  CAAGTCGTGG   300
ATGCGGACCC  AGCAGAAGCG  GGACATCAAG  TTTAGGGAGG  ACTGTCCACA  GGATCGGGAA   360
GAATTGGGTC  GCAACACCTG  GGCTTTCCTT  CATACGCTGG  CCGCCTATTA  CCCGGACATG   420
CCCACGCCAG  AACAACAGCA  GGATATGGCC  CAGTTCATAC  ATATATTTTC  CAAGTTTTAC   480
CCCTGTGAGG  AGTGTGCAGA  AGACATAAGG  AAGAGGATAG  ACAGGAGCCA  GCCAGACACA   540
AGCACTCGAG  TGTCCTTCAG  CCAGTGGCTG  TGCCGCCTTC  ACAATGAAGT  GAACCGGAAG   600
CTGGGCAAGC  CTGATTTTGA  CTGCTCAAGA  GTTGATGAGC  GATGGCGTGA  CGGCTGGAAG   660
GACGGCTCCT  GTGACTAAGG  ATTACCACAG  ACCGTGCAGG  GCAACGCCGG  GTTCTATGGG   720
CAACAGCCTG  ACTGACGATT  AAAGTGCATC  TGAGCCAAAG  CTTGTTTCTG  TGGTGGGGGT   780
GGGATCCCCT  AGAACACTGC  CTATGGGAAC  CCTACCCACA  GACTCAGAAA  CGGAGGTGCC   840
```

| | | | | | |
|---|---|---|---|---|---|
| CACTATAGAC | AGTTGGGTGG | CTTCCTCAGG | TCTTAAAGCC | CCATGGGACT | GAAGATGAGA | 900 |
| GGCAGGAGTG | GTCCAGGGCA | CCCCATACCC | CTTATGATAC | CCATTATACA | TTTGGGACAT | 960 |
| AGTTGCCTCA | AAGGAAGGTG | GGCTAGACCA | TTGCCTTCCT | ACTACATATC | CCCAGCTGCC | 1020 |
| TACAGAACTG | TGACCCAGGC | AACTCTGCCA | TTTCAGAATT | GAAGCAGGGT | TCCAGCTCTA | 1080 |
| GTTGGGTTTT | TCTCTTAGGG | TAAACCAACC | ATGGTGCCCA | CTGTCAGCCT | GGCACATGGT | 1140 |
| CTTCTGCAGC | CAGGACAAAC | ATGTCAGCAG | AGGATCCTGG | GAAGGGCTTC | CTTAGCGTTT | 1200 |
| GAGACCAAAA | TAAAATGAAG | TGACTT | | | | 1226 |

( 2 ) INFORMATION FOR SEQ ID NO:2:

( i ) SEQUENCE CHARACTERISTICS:
        ( A ) LENGTH: 125 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met Arg Thr Gln Gln Lys Arg Asp Ile Lys Phe Arg Glu Asp Cys Pro
 1               5                  10                  15
Gln Asp Arg Glu Glu Leu Gly Arg Asn Thr Trp Ala Phe Leu His Thr
                20                  25                  30
Leu Ala Ala Tyr Tyr Pro Asp Met Pro Thr Pro Glu Gln Gln Gln Asp
                35                  40                  45
Met Ala Gln Phe Ile His Ile Phe Ser Lys Phe Tyr Pro Cys Glu Glu
            50                  55                  60
Cys Ala Glu Asp Ile Arg Lys Arg Ile Asp Arg Ser Gln Pro Asp Thr
 65                 70                  75                  80
Ser Thr Arg Val Ser Phe Ser Gln Trp Leu Cys Arg Leu His Asn Glu
                85                  90                  95
Val Asn Arg Lys Leu Gly Lys Pro Asp Phe Asp Cys Ser Arg Val Asp
                100                 105                 110
Glu Arg Trp Arg Asp Gly Trp Lys Asp Gly Ser Cys Asp
            115                 120                 125
```

( 2 ) INFORMATION FOR SEQ ID NO:3:

( i ) SEQUENCE CHARACTERISTICS:
        ( A ) LENGTH: 375 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
| ATGCGGACCC | AGCAGAAGCG | GGACATCAAG | TTTAGGGAGG | ACTGTCCACA | GGATCGGGAA | 60 |
| GAATTGGGTC | GCAACACCTG | GGCTTTCCTT | CATACGCTGG | CCGCCTATTA | CCCGGACATG | 120 |
| CCCACGCCAG | AACAACAGCA | GGATATGGCC | CAGTTCATAC | ATATATTTTC | CAAGTTTTAC | 180 |
| CCCTGTGAGG | AGTGTGCAGA | AGACATAAGG | AAGAGGATAG | ACAGGAGCCA | GCCAGACACA | 240 |
| AGCACTCGAG | TGTCCTTCAG | CCAGTGGCTG | TGCCGCCTTC | ACAATGAAGT | GAACCGGAAG | 300 |
| CTGGGCAAGC | CTGATTTTGA | CTGCTCAAGA | GTTGATGAGC | GATGGCGTGA | CGGCTGGAAG | 360 |
| GACGGCTCCT | GTGAC | | | | | 375 |

( 2 ) INFORMATION FOR SEQ ID NO:4:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

```
Phe  Tyr  Pro  Xaa  Glu  Glu  Xaa  Ala  Glu  Asp  Ile
 1              5                             10
```

( 2 ) INFORMATION FOR SEQ ID NO:5:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

```
Leu  Gly  Lys  Pro  Asp  Phe  Asp  Xaa  Ser  Xaa  Val
 1              5                             10
```

( 2 ) INFORMATION FOR SEQ ID NO:6:

( i ) SEQUENCE CHARACTERISTICS:
    ( A ) LENGTH: 22 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

```
Xaa  Ile  Asp  Arg  Ser  Gln  Pro  Asp  Thr  Ser  Thr  Arg  Val  Ser  Phe  Xaa
 1              5                             10                            15
Gln  Xaa  Leu  Xaa  Xaa  Leu
                20
```

( 2 ) INFORMATION FOR SEQ ID NO:7:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:7:

AACTGGAAGA ATTCGCGGCC GCAGGAATTT TTTTTTTTT TTTTT     45

( 2 ) INFORMATION FOR SEQ ID NO:8:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:8:

ATNGAYCGNA GYCARCCNGA YAC     23

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

ATNGAYCGNT CNCARCCNGA YAC      23

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

ATNGAYAGRA GYCARCCNGA YAC      23

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

ATNGAYAGRT CNCARCCNGA YAC      23

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Ile Asp Arg Ser Gln Pro Asp Thr
    1                   5

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

GCCGCAGGAA TTTTTTTTTT      20

( 2 ) INFORMATION FOR SEQ ID NO:14:

( i ) SEQUENCE CHARACTERISTICS:
        ( A ) LENGTH: 20 base pairs ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

TGGACTTCAA GTCGTGGATG 20

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GAATTCGATA TCAAGCTTAT CG 22

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

ATGCGGACCC AGCAGAAG 18

( 2 ) INFORMATION FOR SEQ ID NO:17:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

ATTCTGTTTT CCTGTGTGAA ATT 23

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

CTTATCGTCA TCGTCGTACA 20

( 2 ) INFORMATION FOR SEQ ID NO:19:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

| GATCATGGCG | AACAAACACT | TGTCCCTCTC | CCTCTTCCTC | GTCCTCCTTG | GCCTGTCGGC | 60 |
| CAGCTTGGCC | TCCGG | | | | | 75 |

( 2 ) INFORMATION FOR SEQ ID NO:20:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

| CCGGAGGCCA | AGCTGGCCGA | CAGGCCAAGG | AGGACGAGGA | AGAGGGAGAG | GGACAAGTGT | 60 |
| TTGTTCGCCA | T | | | | | 71 |

( 2 ) INFORMATION FOR SEQ ID NO:21:

( i ) SEQUENCE CHARACTERISTICS:
        ( A ) LENGTH: 515 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

| CCGTGCCGGG | CCTGCGTCGA | CTTCAAGACG | TGGATGCGGA | CGCAGCAGAA | GCGGGACACC | 60 |
| AAGTTTAGGG | AGGACTGCCC | GCCGGATCGC | GAGGAACTGG | GCCGCCACAG | CTGGGCTGTC | 120 |
| CTCCACACCC | TGGCCGCCTA | CTACCCCGAC | CTGCCCACCC | CAGAACAGCA | GCAAGACATG | 180 |
| GCCCAGTTCA | TACATTTATT | TTCTAAGTTT | TACCCCTGTG | AGGAGTGTGC | TGAAGACCTA | 240 |
| AGAAAAAGGT | TGTGCAGGAA | CCACCCAGAC | ACCGCACCCC | GGGCATGCTT | CACACAGTGG | 300 |
| CTGTGCCACC | TGCACAATGA | AGTGAACCGC | AAGCTGGGCA | AGCCTGACTT | CGACTGCTCA | 360 |
| AAAGTGGATG | AGCGCTGGCG | CGACGGCTGG | AAGGATGGCT | CCTGTGACTA | GAGGGTGGTC | 420 |
| AGCCAGAGCT | CATGGGACAG | CTAGCCAGGC | ATGGTTGGAT | AGGGGCAGGG | CACTCATTAA | 480 |
| AGTGCATCAC | AGCCAGAAAA | AAAAAAAAA | AAAAA | | | 515 |

( 2 ) INFORMATION FOR SEQ ID NO:22:

( i ) SEQUENCE CHARACTERISTICS:
        ( A ) LENGTH: 375 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

| ATGCGGACGC | AGCAGAAGCG | GGACACCAAG | TTTAGGGAGG | ACTGCCCGCC | GGATCGCGAG | 60 |
| GAACTGGGCC | GCCACAGCTG | GGCTGTCCTC | CACACCCTGG | CCGCCTACTA | CCCCGACCTG | 120 |
| CCCACCCCAG | AACAGCAGCA | AGACATGGCC | CAGTTCATAC | ATTTATTTC | TAAGTTTTAC | 180 |
| CCCTGTGAGG | AGTGTGCTGA | AGACCTAAGA | AAAAGGTTGT | GCAGGAACCA | CCCAGACACC | 240 |
| CGCACCCGGG | CATGCTTCAC | ACAGTGGCTG | TGCCACCTGC | ACAATGAAGT | GAACCGCAAG | 300 |
| CTGGGCAAGC | CTGACTTCGA | CTGCTCAAAA | GTGGATGAGC | GCTGGCGCGA | CGGCTGGAAG | 360 |

GATGGCTCCT GTGAC                                                                    375

( 2 ) INFORMATION FOR SEQ ID NO:23:

( i ) SEQUENCE CHARACTERISTICS:
        ( A ) LENGTH: 125 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

```
Met  Arg  Thr  Gln  Gln  Lys  Arg  Asp  Thr  Lys  Phe  Arg  Glu  Asp  Cys  Pro
 1              5                      10                      15

Pro  Asp  Arg  Glu  Glu  Leu  Gly  Arg  His  Ser  Trp  Ala  Val  Leu  His  Thr
              20                      25                      30

Leu  Ala  Ala  Tyr  Tyr  Pro  Asp  Leu  Pro  Thr  Pro  Glu  Gln  Gln  Gln  Asp
         35                      40                      45

Met  Ala  Gln  Phe  Ile  His  Leu  Phe  Ser  Lys  Phe  Tyr  Pro  Cys  Glu  Glu
 50                           55                      60

Cys  Ala  Glu  Asp  Leu  Arg  Lys  Arg  Leu  Cys  Arg  Asn  His  Pro  Asp  Thr
 65                      70                      75                      80

Arg  Thr  Arg  Ala  Cys  Phe  Thr  Gln  Trp  Leu  Cys  His  Leu  His  Asn  Glu
              85                      90                      95

Val  Asn  Arg  Lys  Leu  Gly  Lys  Pro  Asp  Phe  Asp  Cys  Ser  Lys  Val  Asp
              100                     105                     110

Glu  Arg  Trp  Arg  Asp  Gly  Trp  Lys  Asp  Gly  Ser  Cys  Asp
              115                     120                     125
```

( 2 ) INFORMATION FOR SEQ ID NO:24:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

ATGCGGACGC AGCAGAAGCG GGACA                                                          25

( 2 ) INFORMATION FOR SEQ ID NO:25:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

CTAGTCACAG GAGCCATCCT TCC                                                            23

( 2 ) INFORMATION FOR SEQ ID NO:26:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

Asp Asp Asp Asp Lys
1               5

( 2 ) INFORMATION FOR SEQ ID NO:27:

( i ) SEQUENCE CHARACTERISTICS:
( A ) LENGTH: 727 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:27:

| | | | | | | |
|---|---|---|---|---|---|---|
| CAACATGGCG | GCGCCCGGCG | AGCGGGGCCG | CTTCCACGGC | GGGAACCTCT | TCTTCCTGCC | 60 |
| GGGGGGCGCG | CGCTCCGAGA | TGATGGACGA | CCTGGCGACC | GACGCGCGGG | GCCGGGGCGC | 120 |
| GGGGCGGAGA | GACGCGGCCG | CCTCGGCCTC | GACGCCAGCC | CAGGCGCCGA | CCTCCGATTC | 180 |
| TCCTGTCGCC | GAGGACGCCT | CCCGGAGGCG | GCCGTGCCGG | GCCTGCGTCG | ACTTCAAGAC | 240 |
| GTGGATGCGG | ACGCAGCAGA | AGCGGGACAC | CAAGTTTAGG | GAGGACTGCC | CGCCGGATCG | 300 |
| CGAGGAACTG | GGCCGCCACA | GCTGGGCTGT | CCTCCACACC | CTGGCCGCCT | ACTACCCCGA | 360 |
| CCTGCCCACC | CCAGAACAGC | AGCAAGACAT | GGCCCAGTTC | ATACATTTAT | TTTCTAAGTT | 420 |
| TTACCCCTGT | GAGGAGTGTG | CTGAAGACCT | AAGAAAAAGG | TTGTGCAGGA | ACCACCCAGA | 480 |
| CACCCGCACC | CGGGCATGCT | TCACACAGTG | GCTGTGCCAC | CTGCACAATG | AAGTGAACCG | 540 |
| CAAGCTGGGC | AAGCCTGACT | TCGACTGCTC | AAAAGTGGAT | GAGCGCTGGC | GCGACGGCTG | 600 |
| GAAGGATGGC | TCCTGTGACT | AGAGGGTGGT | CAGCCAGAGC | TCATGGACA | GCTAGCCAGG | 660 |
| CATGGTTGGA | TAGGGGCAGG | GCACTCATTA | AAGTGCATCA | CAGCCAGAAA | AAAAAAAAA | 720 |
| AAAAAAA | | | | | | 727 |

( 2 ) INFORMATION FOR SEQ ID NO:28:

( i ) SEQUENCE CHARACTERISTICS:
( A ) LENGTH: 615 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:28:

| | | | | | | |
|---|---|---|---|---|---|---|
| ATGGCGGCGC | CCGGCGAGCG | GGGCCGCTTC | CACGGCGGGA | ACCTCTTCTT | CCTGCCGGGG | 60 |
| GGCGCGCGCT | CCGAGATGAT | GGACGACCTG | GCGACCGACG | CGCGGGGCCG | GGGCGCGGGG | 120 |
| CGGAGAGACG | CGGCCGCCTC | GGCCTCGACG | CCAGCCCAGG | CGCCGACCTC | CGATTCTCCT | 180 |
| GTCGCCGAGG | ACGCCTCCCG | GAGGCGGCCG | TGCCGGGCCT | GCGTCGACTT | CAAGACGTGG | 240 |
| ATGCGGACGC | AGCAGAAGCG | GGACACCAAG | TTTAGGGAGG | ACTGCCCGCC | GGATCGCGAG | 300 |
| GAACTGGGCC | GCCACAGCTG | GCTGTCCTC | CACACCCTGG | CCGCCTACTA | CCCCGACCTG | 360 |
| CCCACCCCAG | AACAGCAGCA | AGACATGGCC | CAGTTCATAC | ATTTATTTTC | TAAGTTTTAC | 420 |
| CCCTGTGAGG | AGTGTGCTGA | AGACCTAAGA | AAAAGGTTGT | GCAGGAACCA | CCCAGACACC | 480 |
| CGCACCCGGG | CATGCTTCAC | ACAGTGGCTG | TGCCACCTGC | ACAATGAAGT | GAACCGCAAG | 540 |
| CTGGGCAAGC | CTGACTTCGA | CTGCTCAAAA | GTGGATGAGC | GCTGGCGCGA | CGGCTGGAAG | 600 |
| GATGGCTCCT | GTGAC | | | | | 615 |

(2) INFORMATION FOR SEQ ID NO:29:

(i) SEQUENCE CHARACTERISTICS:
(A) LENGTH: 205 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:29:

```
Met Ala Ala Pro Gly Glu Arg Gly Arg Phe His Gly Gly Asn Leu Phe
 1               5                  10                  15
Phe Leu Pro Gly Gly Ala Arg Ser Glu Met Met Asp Asp Leu Ala Thr
            20                  25                  30
Asp Ala Arg Gly Arg Gly Ala Gly Arg Arg Asp Ala Ala Ala Ser Ala
                35                  40                  45
Ser Thr Pro Ala Gln Ala Pro Thr Ser Asp Ser Pro Val Ala Glu Asp
        50                  55                  60
Ala Ser Arg Arg Arg Pro Cys Arg Ala Cys Val Asp Phe Lys Thr Trp
65                  70                  75                  80
Met Arg Thr Gln Gln Lys Arg Asp Thr Lys Phe Arg Glu Asp Cys Pro
                85                  90                  95
Pro Asp Arg Glu Glu Leu Gly Arg His Ser Trp Ala Val Leu His Thr
            100                 105                 110
Leu Ala Ala Tyr Tyr Pro Asp Leu Pro Thr Pro Glu Gln Gln Gln Asp
            115                 120                 125
Met Ala Gln Phe Ile His Leu Phe Ser Lys Phe Tyr Pro Cys Glu Glu
    130                 135                 140
Cys Ala Glu Asp Leu Arg Lys Arg Leu Cys Arg Asn His Pro Asp Thr
145                 150                 155                 160
Arg Thr Arg Ala Cys Phe Thr Gln Trp Leu Cys His Leu His Asn Glu
                165                 170                 175
Val Asn Arg Lys Leu Gly Lys Pro Asp Phe Asp Cys Ser Lys Val Asp
            180                 185                 190
Glu Arg Trp Arg Asp Gly Trp Lys Asp Gly Ser Cys Asp
        195                 200                 205
```

(2) INFORMATION FOR SEQ ID NO:30:

(i) SEQUENCE CHARACTERISTICS:
(A) LENGTH: 540 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:30:

```
ATGATGGACG ACCTGGCGAC CGACGCGCGG GGCCGGGGCG CGGGGCGGAG AGACGCGGCC    60
GCCTCGGCCT CGACGCCAGC CCAGGCGCCG ACCTCCGATT CTCCTGTCGC CGAGGACGCC   120
TCCCGGAGGC GGCCGTGCCG GGCCTGCGTC GACTTCAAGA CGTGGATGCG GACGCAGCAG   180
AAGCGGGACA CCAAGTTTAG GGAGGACTGC CCGCCGGATC GCGAGGAACT GGGCCGCCAC   240
AGCTGGGCTG TCCTCCACAC CCTGGCCGCC TACTACCCCG ACCTGCCCAC CCCAGAACAG   300
CAGCAAGACA TGGCCCAGTT CATACATTTA TTTTCTAAGT TTTACCCCTG TGAGGAGTGT   360
GCTGAAGACC TAAGAAAAAG GTTGTGCAGG AACCACCCAG ACACCCGCAC CCGGGCATGC   420
TTCACACAGT GGCTGTGCCA CCTGCACAAT GAAGTGAACC GCAAGCTGGG CAAGCCTGAC   480
```

TTCGACTGCT CAAAAGTGGA TGAGCGCTGG CGCGACGGCT GGAAGGATGG CTCCTGTGAC       540

( 2 ) INFORMATION FOR SEQ ID NO:31:

( i ) SEQUENCE CHARACTERISTICS:
        ( A ) LENGTH: 180 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
Met Met Asp Asp Leu Ala Thr Asp Ala Arg Gly Arg Gly Ala Gly Arg
 1               5                  10                 15

Arg Asp Ala Ala Ala Ser Ala Ser Thr Pro Ala Gln Ala Pro Thr Ser
             20                  25                 30

Asp Ser Pro Val Ala Glu Asp Ala Ser Arg Arg Arg Pro Cys Arg Ala
         35                  40                 45

Cys Val Asp Phe Lys Thr Trp Met Arg Thr Gln Gln Lys Arg Asp Thr
     50              55                  60

Lys Phe Arg Glu Asp Cys Pro Pro Asp Arg Glu Glu Leu Gly Arg His
 65              70                  75                 80

Ser Trp Ala Val Leu His Thr Leu Ala Ala Tyr Tyr Pro Asp Leu Pro
                 85                  90                 95

Thr Pro Glu Gln Gln Gln Asp Met Ala Gln Phe Ile His Leu Phe Ser
                100                 105                110

Lys Phe Tyr Pro Cys Glu Glu Cys Ala Glu Asp Leu Arg Lys Arg Leu
             115                 120                125

Cys Arg Asn His Pro Asp Thr Arg Thr Arg Ala Cys Phe Thr Gln Trp
     130                 135                 140

Leu Cys His Leu His Asn Glu Val Asn Arg Lys Leu Gly Lys Pro Asp
145                 150                 155                160

Phe Asp Cys Ser Lys Val Asp Glu Arg Trp Arg Asp Gly Trp Lys Asp
                 165                 170                175

Gly Ser Cys Asp
             180
```

( 2 ) INFORMATION FOR SEQ ID NO:32:

( i ) SEQUENCE CHARACTERISTICS:
        ( A ) LENGTH: 537 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

ATGGACGACC TGGCGACCGA CGCGCGGGGC CGGGGCGCGG GGCGGAGAGA CGCGGCCGCC       60

TCGGCCTCGA CGCCAGCCCA GGCGCCGACC TCCGATTCTC CTGTCGCCGA GGACGCCTCC      120

CGGAGGCGGC CGTGCCGGGC CTGCGTCGAC TTCAAGACGT GGATGCGGAC GCAGCAGAAG      180

CGGGACACCA AGTTTAGGGA GGACTGCCCG CCGGATCGCG AGGAACTGGG CCGCCACAGC      240

TGGGCTGTCC TCCACACCCT GGCCGCCTAC TACCCCGACC TGCCCACCCC AGAACAGCAG      300

CAAGACATGG CCCAGTTCAT ACATTTATTT CTAAGTTTT ACCCCTGTGA GGAGTGTGCT       360

GAAGACCTAA GAAAAAGGTT GTGCAGGAAC CACCCAGACA CCCGCACCCG GGCATGCTTC      420

ACACAGTGGC TGTGCCACCT GCACAATGAA GTGAACCGCA AGCTGGGCAA GCCTGACTTC      480

```
GACTGCTCAA  AAGTGGATGA  GCGCTGGCGC  GACGGCTGGA  AGGATGGCTC  CTGTGAC                537
```

( 2 ) INFORMATION FOR SEQ ID NO:33:

( i ) SEQUENCE CHARACTERISTICS:
        ( A ) LENGTH: 179 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

```
Met  Asp  Asp  Leu  Ala  Thr  Asp  Ala  Arg  Gly  Arg  Gly  Ala  Gly  Arg  Arg
 1              5                             10                       15

Asp  Ala  Ala  Ala  Ser  Ala  Ser  Thr  Pro  Ala  Gln  Ala  Pro  Thr  Ser  Asp
                20                       25                       30

Ser  Pro  Val  Ala  Glu  Asp  Ala  Ser  Arg  Arg  Arg  Pro  Cys  Arg  Ala  Cys
           35                       40                       45

Val  Asp  Phe  Lys  Thr  Trp  Met  Arg  Thr  Gln  Gln  Lys  Arg  Asp  Thr  Lys
      50                       55                       60

Phe  Arg  Glu  Asp  Cys  Pro  Pro  Asp  Arg  Glu  Glu  Leu  Gly  Arg  His  Ser
 65                       70                       75                       80

Trp  Ala  Val  Leu  His  Thr  Leu  Ala  Ala  Tyr  Tyr  Pro  Asp  Leu  Pro  Thr
                85                       90                       95

Pro  Glu  Gln  Gln  Gln  Asp  Met  Ala  Gln  Phe  Ile  His  Leu  Phe  Ser  Lys
                100                      105                      110

Phe  Tyr  Pro  Cys  Glu  Glu  Cys  Ala  Glu  Asp  Leu  Arg  Lys  Arg  Leu  Cys
           115                      120                      125

Arg  Asn  His  Pro  Asp  Thr  Arg  Thr  Arg  Ala  Cys  Phe  Thr  Gln  Trp  Leu
      130                      135                      140

Cys  His  Leu  His  Asn  Glu  Val  Asn  Arg  Lys  Leu  Gly  Lys  Pro  Asp  Phe
145                       150                      155                      160

Asp  Cys  Ser  Lys  Val  Asp  Glu  Arg  Trp  Arg  Asp  Gly  Trp  Lys  Asp  Gly
                165                      170                      175

Ser  Cys  Asp
```